(12) United States Patent
Neamati et al.

(10) Patent No.: US 7,947,682 B2
(45) Date of Patent: *May 24, 2011

(54) SUBSTITUTED N'-PYRROLO[1,2-A]QUINOXALIN-4-YL-HYDRAZIDES AS ANTI-CANCER AGENTS

(75) Inventors: Nouri Neamati, Fullerton, CA (US); Antonio Garofalo, Siena (IT)

(73) Assignee: University of Southern California, Los Angeles, CA (US)

( * ) Notice: Subject to any disclaimer, the term of this patent is extended or adjusted under 35 U.S.C. 154(b) by 1215 days.

This patent is subject to a terminal disclaimer.

(21) Appl. No.: 11/027,465

(22) Filed: Dec. 29, 2004

(65) Prior Publication Data

US 2006/0142294 A1    Jun. 29, 2006

(51) Int. Cl.
C07D 487/04    (2006.01)
A61K 31/519    (2006.01)
A61P 35/04    (2006.01)

(52) U.S. Cl. ........................ 514/250; 544/346

(58) Field of Classification Search ............... 514/250
See application file for complete search history.

(56) References Cited

U.S. PATENT DOCUMENTS 6,077,869 A    6/2000    Sui et al. ............ 514/615
6,635,641 B2 *  10/2003   Bender et al. ......... 514/247

FOREIGN PATENT DOCUMENTS

WO    WO 02/02593    *   1/2002

OTHER PUBLICATIONS

Freshney (Culture of Animal Cells, A Manual of Basic Technique, Alan R. Liss, Inc., 1983, New York, p. 4).*
Dermer, Gerald B., downloaded <http//www.virusmyth.com/aids/hiv/gdbiotech.htm> on Mar. 14, 2010.*
M.M. Badran et al., "Synthesis of Certain Novel 3-Substituted Coumarins," *Bull. Fac. Pharm. Cairo Univ.*, vol. 28, No. 2., pp. 39-42 (1990).
Campiani et al., "Quinoxalinylethylpyridylthioureas (QXPTs) as Potent Non-Nucleoside HIV-1 Reverse Transcriptase (RT) Inhibi-tors. Further SAR Studies and Identification of a Novel Orally Bioavailable Hydrazine-Based Antiviral Agent," *J. Med. Chem.*, vol. 44, pp. 305-315 (2001).
Sonal Shah et al., "Synthesis, Characterisation and Screening of some New Hydrazides and 2-Aryl-5-(8'-methoxycoumarin-3'-yl)-1,3,4-oxadiazoles as Antibacterial Agents," *J. Indian Chem.Soc.*, vol. 74, Mar. 1997, pp. 241-242.
International Search Report and Written Opinion of the International Search Authority : for PCT/US05/39687, Prepared Apr. 20, 2006.
Data from the DTP Datawarehouse, from the Developmental Therapeutics Program, *National Cancer Institute*, DTP Datawarehouse Index Results of Compound NSC 711679, generated Mar. 31, 2008.
Data from the DTP Datawarehouse, from the Developmental Therapeutics Program, *National Cancer Institute*, DTP Datawarehouse Index Results of Compound NSC 711683, generated Mar. 31, 2008.

* cited by examiner

*Primary Examiner* — Susanna Moore
(74) *Attorney, Agent, or Firm* — DLA Piper LLP (US)

(57) ABSTRACT

Novel compounds for treatment of cancer and disorders associated with angiogenesis function. Such compounds include a compound of Formula II,

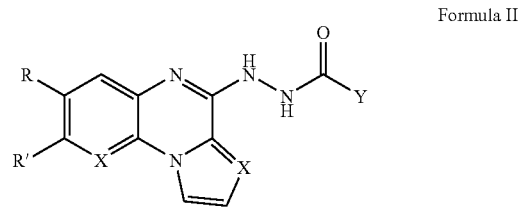

Formula II wherein
R is H, alkyl, or halogen;
R' is H, alkyl, or halogen;
X is CH or N; and
Y comprises a homocyclic or heterocyclic ring.

Also disclosed are a method of preparing the compounds, pharmaceutical compositions and packaged products containing the compounds, a method of using these molecules to treat cancer (e.g., leukemia, non-small cell lung cancer, colon cancer, CNS cancer, melanoma, ovarian cancer, breast cancer, renal cancer, and prostate cancer) and disorders associated with angiogenesis function (e.g., age-related macular degeneration, macular dystrophy, and diabetes), a method of monitoring the treatment, a method of profiling gene expression, and a method of modulating gene expression.

4 Claims, 15 Drawing Sheets

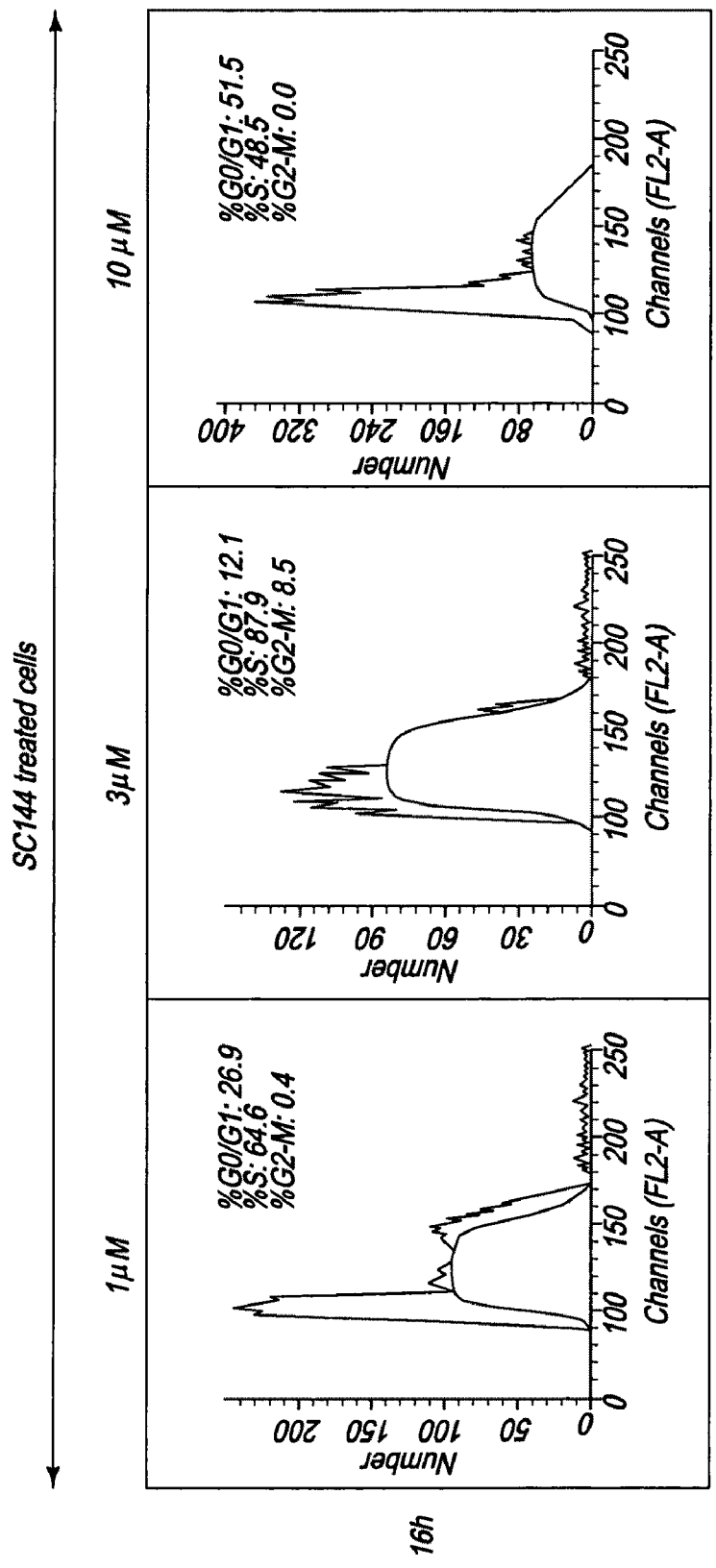
FIG. 1 (Part 1/4)

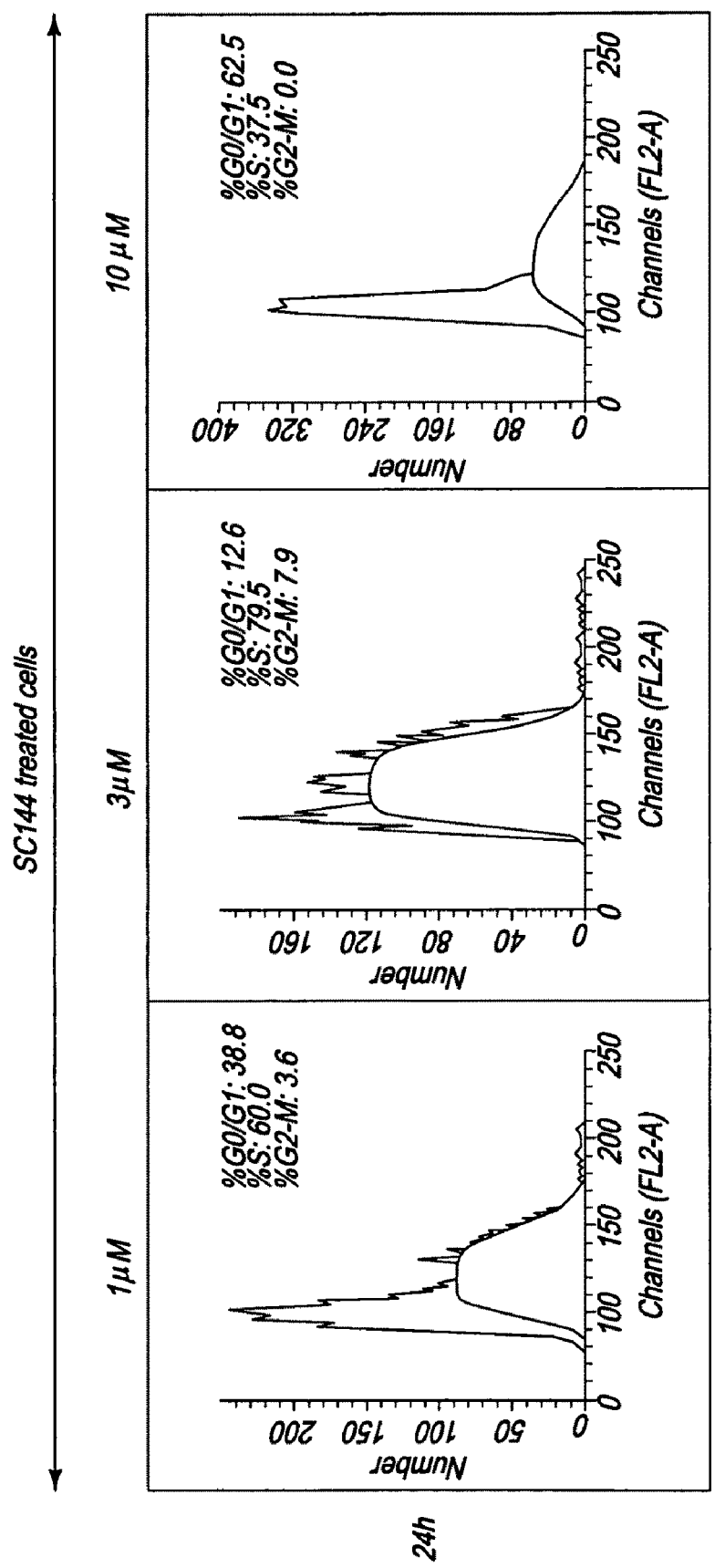
FIG. 1 (Part 2/4)

(Part 3/4)

(Part 4/4)

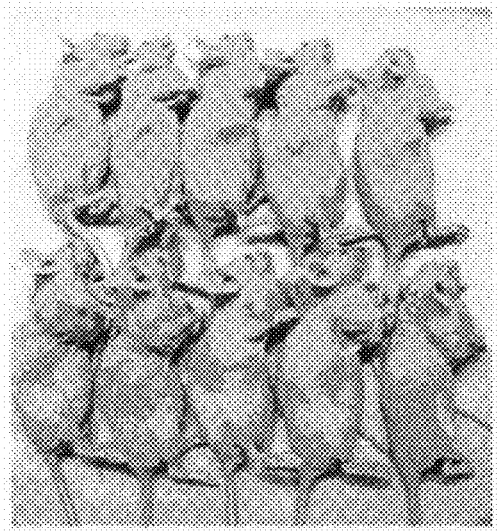
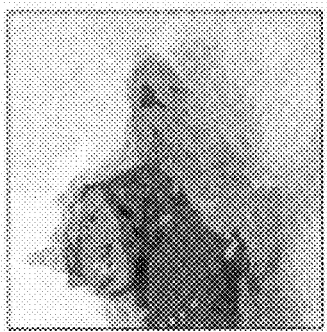 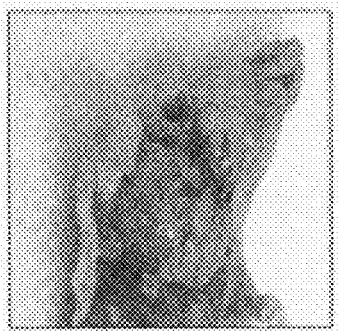
FIGURE 4

| Category | Attribute | OR | p-value |
|---|---|---|---|
| Molecular function | Monophenol monooxygenase | inf | <0.0001 |
| Biologic process | Developmental process | 3.0 | <0.0001 |
| Cellular component | Integral membrane protein | 2.2 | <0.0001 |
| InterPro | EGF-like domain | 7.1 | <0.0001 |
| SCOP | All alpha proteins- Di- copper centre-containing domain | inf | <0.0001 |
| Pathway | Signal Transduction | 4.2 | 0.0079 |
| Chromosome band | 9p | 7.1 | <0.0001 |
| Subset | Etoposide 10xfold | 16.1 | <0.0001 |

*FIG. 11*

| Integrin, beta 3 (platelet glycoprotein IIIa, antigen CD61) |
|---|
| MEGF10 protein<br>EphA2<br>Jagged 1 (Alagille syndrome)<br>Hemicentin<br>Diphtheria toxin receptor (heparin-binding epidermal growth factor-like growth factor)<br>Low density lipoprotein receptor (familial hypercholesterolemia)<br>Tyrosinase-related protein 1<br>Tyrosinase (oculocutaneous albinism IA)<br>A disintegrin and metalloproteinase domain 19 (meltrin beta)<br>Dopachrome tautomerase (dopachrome delta-isomerase, tyrosine-related protein 2)<br>Laminin, beta 3 |

*FIG. 12*

| Methionine-tRNA synthetase |
|---|
| MAX dimerization protein 1
CDK4-binding protein p34SEI1
Homo sapiens cDNA FLJ42435 fis, clone BLADE2006849
AXIN1 up-regulated 1
Growth arrest and DNA-damage-inducible, beta
Cyclin-dependent kinase inhibitor 2B (p15, inhibits CDK4)
Sestrin 2
Diphtheria toxin receptor (heparin-binding epidermal growth factor-like growth factor)
GTP binding protein overexpressed in skeletal muscle
Hypothetical protein MGC4504
Syntaxin binding protein 6 (amisyn)
Transport-secretion protein 2.2
Arg/Abl-interacting protein ArgBP2
Hypothetical protein DJ667H12.2
Cyclin-dependent kinase inhibitor 1A (p21, Cip1)
Homo sapiens cDNA FLJ37284 fis, clone BRAMY2013590.
Hypothetical protein DKFZp434L142 |

FIG. 13

⊟·SUBSET    (33 :   5.39 : <0.000001)
    ┆--- Mitoxantrone 10x fold    (9 :   8.67 : 0.000005)
    ┆--- Etoposide 10xfold    (19 :  16.13 : <0.000001)
    ┆--- Cisplatin 10x fold    (1 :   1.73 : 0.89)
    ┆--- Taxol 10x fold    (0 :   0.00 : 0.85)
    ┆--- 5FU 10x fold    (1 :   0.77 : 1.00)
    ┆--- CPT 10x fold    (16 :   3.35 : 0.000001)

Figure 14

SUBSTITUTED N'-PYRROLO[1,2-A]QUINOXALIN-4-YL-HYDRAZIDES AS ANTI-CANCER AGENTS

FIELD OF THE INVENTION

The present invention relates to therapeutic compounds for treatment of cancer and disorders associated with angiogenesis function. More specifically, the invention relates to novel compounds and their uses in treating cancer such as leukemia, non-small cell lung cancer, colon cancer, CNS cancer, melanoma, ovarian cancer, breast cancer, renal cancer, and prostate cancer, as well as disorders associated with angiogenesis function such as age-related macular degeneration, macular dystrophy, and diabetes.

BACKGROUND OF THE INVENTION

Traditionally most anticancer drugs were discovered by high throughput screening with cytotoxicity as the end-point measurement (Neamati and Barchi Jr. (2002) Curr. Top. Med. Chem 2:211-227). In general, most if not all of these drugs have multiple mechanisms of action and multiple mechanisms of resistance. With very few exceptions, their mechanisms of action were identified much later than their discovery. True mechanisms of action of certain drugs were found to be different than what they originally anticipated. Although various strategies have been used to identify drug targets, it is becoming appreciated that there are no easy and straightforward ways to do so with current technologies. Two reasons can be presented to explain this phenomenon. The first has to do with the intrinsic natures of small molecule drugs (e.g., membrane permeability in many cell types) coupled with their lack of selectivity and specificity as compared to for example, antibody-antigen recognition. Second, there is an overwhelming redundancy built into the biological systems serving as targets, due to the abundance of sequence and structural homology. This might explain why in many cases "messy anticancer drugs" work just as well or better than targeted therapeutics. Whatever the mechanism, an initial and critical step in any drug discovery program is lead identification.

Of over 100 FDA approved anticancer drugs, fewer than 20 are widely used. By contrast, all the 19 FDA approved drugs for HIV-1 infection are used in various combinations. Although antiviral drugs are almost always administered orally, only very few anticancer drugs are orally active. Accordingly, it is desirable that most targeted therapeutics of the future are orally active.

SUMMARY OF THE INVENTION

This invention is based, at least in part, on the unexpected discovery that novel compounds described below can be used for treating cancer and disorders associated with angiogenesis function.

Accordingly, in one aspect, the invention features a compound of Formula I,

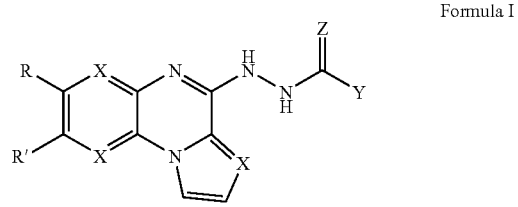

Formula I wherein X=CH or N; Z=O or S; R=alkyl, halogen, acetyl, O-alkyl, or N-alkyl; R'=alkyl, halogen, acetyl, O-alkyl, or N-alkyl; and Y=alkyl, heterocyclic aromatic, aliphatic, sugar, or lipid.

In another aspect, the invention features a compound of Formula II,

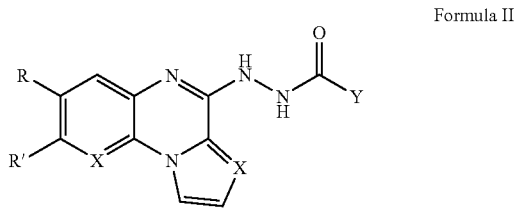

Formula II wherein R is H, alkyl, or halogen; R' is H, alkyl, or halogen; X is CH or N; and Y comprises a homocyclic or heterocyclic ring, wherein Y is 2-pyrazinyl or 2-, 3-, 4-pyridinyl when R is H, R' is H, X is CH, and Y is pyrazinyl or pyridinyl.

For example, the alkyl may be Me, the halogen may be F, and Y may be pyrrolyl, pyridinyl, pyrazinyl, fluorophenyl, quinoxalinyl, or pyrrolo-quinoxalinyl. More specifically, in one embodiment, R is H, R' is H, and X is CH; in another embodiment, R is Me, R' is Me, and X is CH; in still another embodiment, R is F, R' is H, and X is CH; and in yet another embodiment, R is H, R' is H, and X is N. Examples of such compounds include SC141, SC142, SC143, SC144, SC148, SC166, SC167, SC168, SC169, SC170, SC171, SC172, SC173, and SC174.

SC141

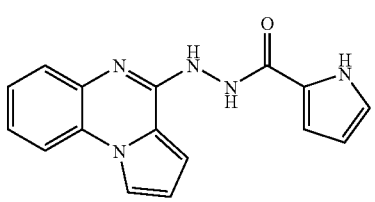

1H-Pyrrole-2-carboxylic acid N'-pyrrolo[1,2-a]quinoxalin-4-yl-hydrazide

-continued

| | | |
|---|---|---|
| SC142 | | Nicotinic acid N'-pyrrolo[1,2-a]quinoxalin-4-yl-hydrazide |
| SC143 | | Pyrazine-2-carboxylic acid N'-(7,8-dimethyl-pyrrolo[1,2-a]quinoxalin-4-yl)-hydrazide |
| SC144 | | Pyrazine-2-carboxylic acid N'-(7-fluoro-pyrrolo[1,2-a]quinoxalin-4-yl)-hydrazide |
| SC148 | | N'-Imidazo[1,2-a]pyrido[3,2-e]pyrazin-6-ylpyrazine-2-carbohydrazide |
| SC166 | | 2-Fluoro-benzoic acid N'-pyrrolo[1,2-a]quinoxalin-4-yl-hydrazide |
| SC167 | | 2-Fluoro-5-hydroxy-benzoic acid N'-pyrrolo[1,2-a]quinoxalin-4-yl-hydrazide |
| SC168 | | 3-Fluoro-benzoic acid N'-pyrrolo[1,2-a]quinoxalin-4-yl-hydrazide |
| SC169 | | 3-Fluoro-5-trifluoromethyl-benzoic acid N'-pyrrolo[1,2-a]quinoxalin-4-yl-hydrazide |

-continued
SC170 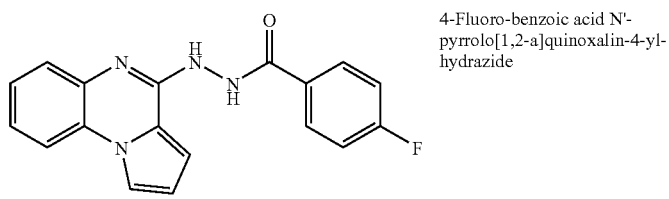 4-Fluoro-benzoic acid N'-pyrrolo[1,2-a]quinoxalin-4-yl-hydrazide
SC171 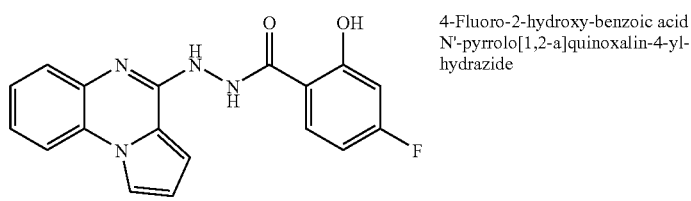 4-Fluoro-2-hydroxy-benzoic acid N'-pyrrolo[1,2-a]quinoxalin-4-yl-hydrazide
SC172 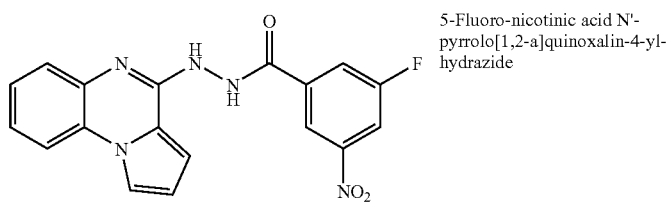 5-Fluoro-nicotinic acid N'-pyrrolo[1,2-a]quinoxalin-4-yl-hydrazide
SC173 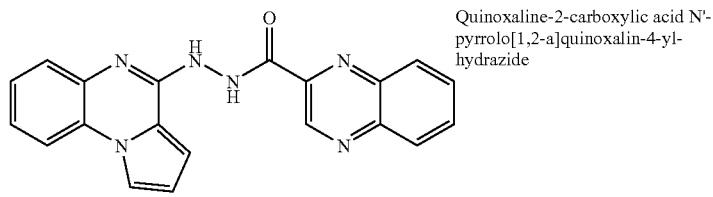 Quinoxaline-2-carboxylic acid N'-pyrrolo[1,2-a]quinoxalin-4-yl-hydrazide
SC174 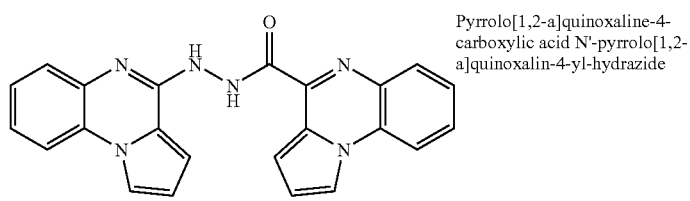 Pyrrolo[1,2-a]quinoxaline-4-carboxylic acid N'-pyrrolo[1,2-a]quinoxalin-4-yl-hydrazide In one embodiment, the compound is of Formula III, Formula III

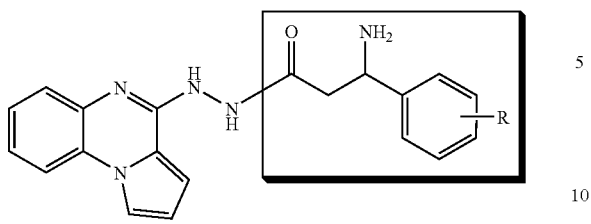

wherein R=o-Cl, p-Cl, p-F, p-CN, p-OMe, or p-CF$_3$. Examples of such compounds include SC160, SC161, SC162, SC163, SC164, and SC165.

| SC160 | 3-Amino-3-(2-chloro-phenyl)-propionic acid N'-pyrrolo[1,2-a]quinoxalin-4-yl-hydrazide |
| SC161 | 3-Amino-3-(4-chloro-phenyl)-propionic acid N'-pyrrolo[1,2-a]quinoxalin-4-yl-hydrazide |
| SC162 | 3-Amino-3-(4-fluoro-phenyl)-propionic acid 4'-pyrrolo[1,2-a]quinoxalin-4-yl-hydrazide |
| SC163 | 3-Amino-3-(4-cyano-phenyl)-propionic acid N'-pyrrolo[1,2-a]quinoxalin-4-yl-hydrazide |
| SC164 | 3-Amino-3-(4-methoxy-phenyl)-propionic acid N'-pyrrolo[1,2-a]quinoxalin-4-yl-hydrazide |
| SC165 | 3-Amino-3-(4-trifluoromethyl-phenyl)-propionic acid N'-pyrrolo[1,2-a]quinoxalin-4-yl-hydrazide |

In another embodiment, the compound is of Formula IV,

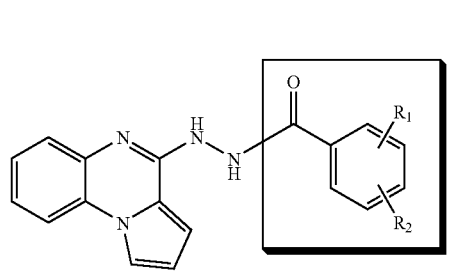

Formula IV wherein R₁=3-NH₂, R₂=5-CF₃; R₁=5-NH₂, R₂=2-NO₂; R₁=4-NH₂, R₂=3-NO₂; R₁=2-NH₂, R₂=5-OH; R₁=4-NH₂, R₂=H; R₁=3-NH₂, R₂=H; or R₁=2-NH₂, R₂=H.

The invention also features a compound of Formula V,

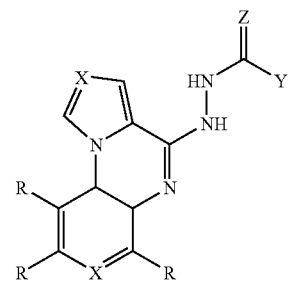

Formula V wherein X=CH or N; Z=O or S; R=alkyl, halogen, acetyl, O-alkyl, or N-alkyl; and Y=alkyl, heterocyclic aromatic, aliphatic, sugar, or lipid. Examples of such compounds include SC153, SC154, SC155, SC156, SC157, and SC158.

| | | |
|---|---|---|
| SC153 | 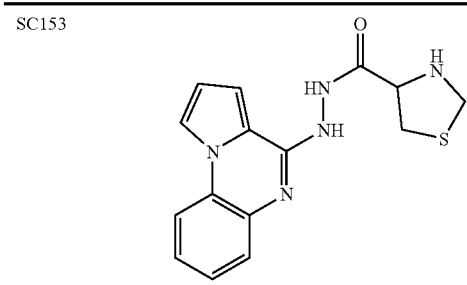 | Thiazolidine-4-carboxylic acid N'-pyrrolo[1,2-a]quinoxalin-4-yl-hydrazide |
| SC154 | 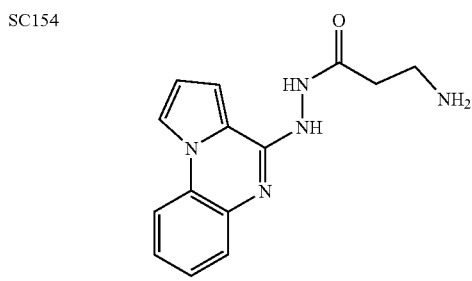 | 3-Amino-propionic acid N'-pyrrolo[1,2-a]quinoxalin-4-yl-hydrazide |
| SC155 | 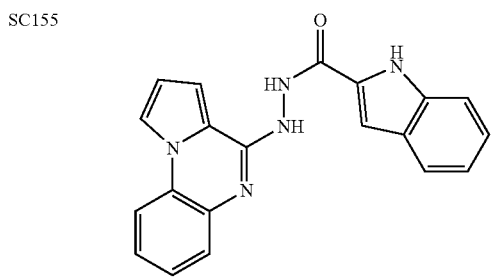 | 1H-Indole-2-carboxylic acid N'-pyrrolo[1,2-a]quinoxalin-4-yl-hydrazide |
| SC156 | 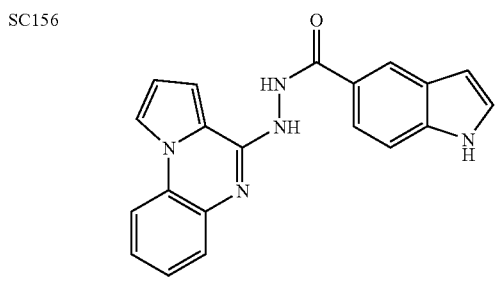 | 1H-Indole-5-carboxylic acid N'-pyrrolo[1,2-a]quinoxalin-4-yl-hydrazide |

| | | -continued |
|---|---|---|
| SC157 | 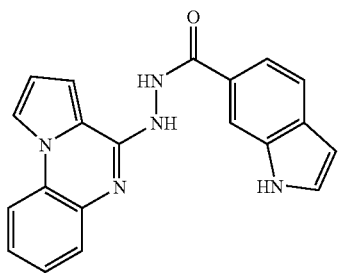 | 1H-Indole-6-carboxylic acid N'-pyrrolo[1,2-a]quinoxalin-4-yl-hydrazide |
| SC158 | 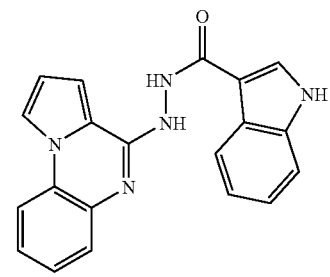 | 1H-Indole-3-carboxylic acid N'-pyrrolo[1,2-a]quinoxalin-4-yl-hydrazide |

Another compound of the invention is of Formula VI,

Formula VI

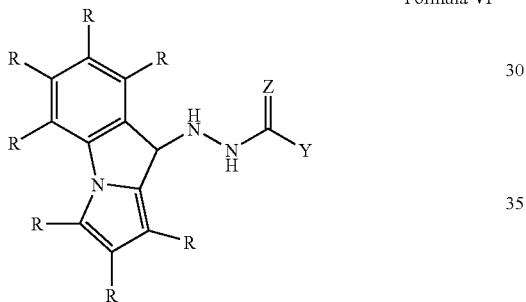

wherein Z=O or S; R=alkyl, halogen, acetyl, O-alkyl, or N-alkyl; and Y=alkyl, heterocyclic aromatic, aliphatic, sugar, or lipid. Examples of such compounds include SC175 and SC176.

| SC175 | 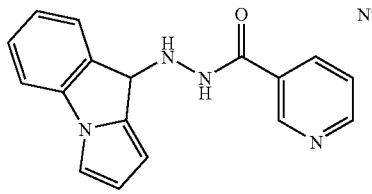 | N'-9H-pyrrolo[1,2-a]indol-9-ylnicotinohydrazide |
|---|---|---|
| SC176 | 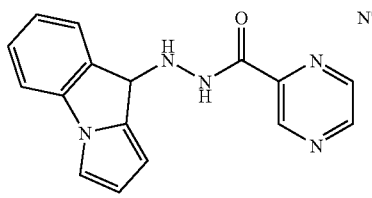 | N'-9H-pyrrolo[1,2-a]indol-9-ylpyrazine-2-carbohydrazide |

Moreover, a compound of Formula VII is also within the invention:

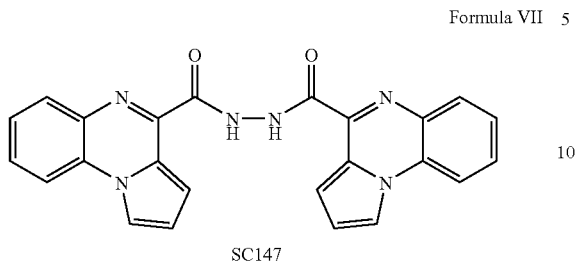

Formula VII

SC147

The invention provides a method of preparing the compounds of the invention. For example, compounds SC141-144, SC148, SC153-158, and SC160-174 can be prepared as follows: First, contact hydrazine monohydrate with a compound (13a, 13b, 13c, or 13d) of Formula VIII,

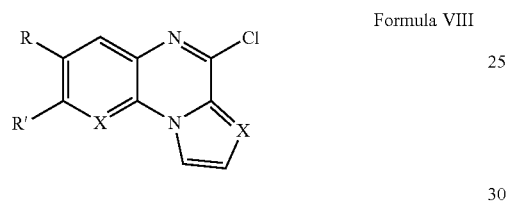

Formula VIII wherein R is H, R' is H, and X is CH (13a); R is Me, R' is Me, and X is CH (13b); R is F, R' is H, and X is CH (13c); or R is H, R' is H, and X is N (13d), to form a compound (14a, 14b, 14c, or 14d, respectively) of Formula IX,

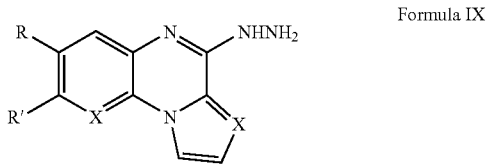

Formula IX wherein R is H, R' is H, and X is CH (14a); R is Me, R' is Me, and X is CH (14b); R is F, R' is H, and X is CH (14c); or R is H, R' is H, and X is N (14d). SC141 can then be formed by contacting 14a with pyrrole-2-carboxylic acid chloride; SC142 by contacting 14a with nicotinoyl chloride hydrochloride; SC143, SC144, and SC148 by contacting 14b, 14c, and 14d with 2-pyrazinecarboxylic acid in the presence of 2,2'-dipyrildisulphide and triphenylphosphine, respectively; SC153 by contacting 14a with N—BOC-thiazolidine-4-carboxylic acid in the presence of 1-[3-(dimethylamino)propyl]-3-ethylcarbodiimide hydrochloride (EDC)/4-(dimethylamino)pyridine (DMAP) and then trifluoroacetic acid (TFA)/anisole; SC154 by contacting 14a with N—BOC-β-alanine in the presence of EDC/DMAP and then TFA/anisole; SC155, SC156, SC157, and SC158 by contacting 14a with 2-indolecarboxylic acid, 5-indolecarboxylic acid, 6-indolecarboxylic acid, and 3-indolecarboxylic acid in the presence of EDC/DMAP, respectively; SC160, SC161, SC162, SC163, SC164, and SC165 by contacting 14a with Boc-3-amino-3-(2-chlorophenyl)propionic acid, Boc-3-amino-3-(4-chlorophenyl)propionic acid, Boc-3-amino-3-(4-fluorophenyl)propionic acid, Boc-3-amino-3-(4-cyanophenyl)propionic acid, Boc-3-amino-3-(4-methoxyphenyl)propionic acid, and Boc-3-amino-3-(4-trifluoromethylphenyl)propionic acid in the presence of EDC/DMAP followed by TFA and anisole, respectively; SC166, SC167, SC168, SC169, SC170, SC171, and SC172 by contacting 14a with 15a-g (15a: 2-fluorobenzoic acid, 15b: 2-fluoro-4-hydroxybenzoic acid, 15c: 3-fluorobenzoic acid, 15d: 3-fluoro-4-(trifluoromethyl)benzoic acid, 15e: 4-fluorobenzoic acid, 15f: 4-fluoro-2-hydroxybenzoic acid, 15 g: 3-fluoro-5-nitrobenzoic acid), respectively, in the presence of EDC/DMAP followed by TFA and anisole, respectively; SC173 by contacting 14a with 2-quinoxalinecarboxylic acid, dichloromethane, triphenylphosphine, and 2,2'dipyridyl disulfide; and SC174 by contacting 14a with pyrrolo[1,2-α]quinoxaline-4-carboxylic acid, dichloromethane, triphenylphosphine, and 2,2'-dipyridyl disulfide.

Compound SC147 can be prepared by contacting hydrazine monohydrate with a compound of formula X.

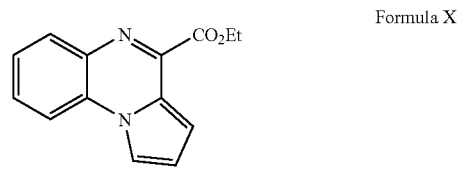

Formula X

Compound SC175 can be prepared by contacting nicotinoyl chloride hydrochloride with 9-hydrazino-9H-pyrrolo[1,2-α] indole and pyridine. Compound SC176 can be prepared by contacting 2-pyrazinecarboxylic acid with 9-hydrazino-9H-pyrrolo[1,2-α]indole.

The invention further provides a pharmaceutical composition comprising an effective amount of a compound of the invention and a pharmaceutically acceptable carrier. The composition may further comprise an effective amount of one or more other agents for treating cancer or a disorder associated with angiogenesis function, e.g., taxol, doxorubicin, or 5-FU.

The invention also features a packaged product comprising a container; an effective amount of a compound of formula XI or XII,

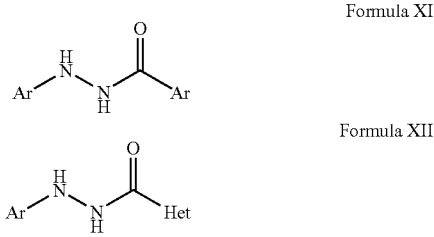

Formula XI

Formula XII wherein Ar comprises an aromatic ring and Het comprises a heterocyclic ring; and an insert associated with the container, indicating administering the compound for treating non-small cell lung cancer, CNS cancer, ovarian cancer, breast cancer, renal cancer, prostate cancer, age-related macular degeneration, macular dystrophy, or diabetes.

Furthermore, the invention provides a packaged product comprising a container; an effective amount of a compound of Formula II,

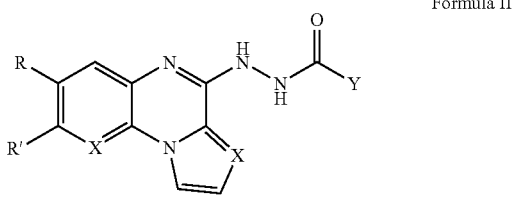

Formula II wherein R is H, alkyl, or halogen; R' is H, alkyl, or halogen; X is CH or N; and Y comprises a homocyclic or heterocyclic ring; and an insert associated with the container, indicating administering the compound for treating cancer or a disorder associated with angiogenesis function.

Another packaged product comprises a container; an effective amount of a compound of the invention; and an insert associated with the container, indicating administering the compound for treating cancer or a disorder associated with angiogenesis function.

A product of the invention may further comprise an effective amount of one or more other agents for treating cancer or a disorder associated with angiogenesis function, e.g., taxol, doxorubicin, or 5-FU.

Examples of cancer include leukemia, non-small cell lung cancer, colon cancer, CNS cancer, melanoma, ovarian cancer, breast cancer, renal cancer, and prostate cancer; examples of disorders associated with angiogenesis function include age-related macular degeneration, macular dystrophy, and diabetes.

Also within the scope of the invention is a method of treating a subject by administering to a subject in need thereof an effective amount of a compound described above. The subject may be identified as being suffering from or at risk for developing cancer or a disorder associated angiogenesis function. In particular, the cancer may be leukemia, non-small cell lung cancer, colon cancer, CNS cancer, melanoma, ovarian cancer, breast cancer, renal cancer, or prostate cancer; and the disorder associated with angiogenesis function may be age-related macular degeneration, macular dystrophy, or diabetes. The method may further comprise administering to the subject an effective amount of one or more other agents for treating cancer or a disorder associated with angiogenesis function, e.g., taxol, doxorubicin, or 5-FU. The compound and the one or more other agents may be administered simultaneously or sequentially.

In addition, the invention features a method of monitoring treatment of a subject by administering to a subject having cancer cells or cells associated with an angiogenesis function disorder a compound described above and measuring the survival of the cells, the growth of the cells, or a combination thereof using PET imaging. The subject may be suffering from leukemia, non-small cell lung cancer, colon cancer, CNS cancer, melanoma, ovarian cancer, breast cancer, renal cancer, prostate cancer, age-related macular degeneration, macular dystrophy, or diabetes. The subject may be an animal, e.g., a mouse, and the cells may be xenografted human cells. In one embodiment, the subject is a human.

Furthermore, the invention provides a method of profiling gene expression. The method comprises contacting a test cell with a compound described above and profiling gene expression in the test cell. The test cell may be a cancer cell or a cell associated with an angiogenesis function disorder. More specifically, the test cell may be a leukemia cell, non-small cell lung cancer cell, colon cancer cell, CNS cancer cell, melanoma cell, ovarian cancer cell, breast cancer cell, renal cancer cell, prostate cancer cell; or a cell associated with age-related macular degeneration, macular dystrophy, or diabetes. The method may further comprise comparing gene expression in the test cell with that in a control cell, which may be contacted with another compound with known action or resistant to the compound used to contact the test cell.

The invention also provides a method of modulating gene expression in a cell. The method comprises contacting a cell with a compound described above, thereby modulating expression of one or more genes in the cell. The cell may be a cancer cell or a cell associated with an angiogenesis function disorder. Specifically, the cell may be a leukemia cell, non-small cell lung cancer cell, colon cancer cell, CNS cancer cell, melanoma cell, ovarian cancer cell, breast cancer cell, renal cancer cell, prostate cancer cell; or a cell associated with age-related macular degeneration, macular dystrophy, or diabetes. Examples of the one or more genes include small proline-rich protein 1A; GTP binding protein overexpressed in skeletal muscle; interleukin 24; sestrin 2; hypothetical protein MGC4504; cyclin-dependent kinase inhibitor 1A (p21); early growth response 1; ATPase, H+transporting, lysosomal 38 kDa, V0 subunit d isoform 2; AXIN1 up-regulated 1; dual specificity phosphatase 5; superoxide dismutase 2, mitochondrial; heparin-binding epidermal growth factor-like growth factor; A disintegrin and metalloproteinase domain 19 (meltrin beta); endothelial PAS domain protein 1; inositol 1,4,5-triphosphate receptor, type 1; tissue factor pathway inhibitor (lipoprotein-associated coagulation inhibitor); fibrinogen, gamma polypeptide; RAB20, member RAS oncogene family; protein kinase, AMP-activated, gamma 2 non-catalytic subunit; oncostatin M receptor; cathepsin B; nuclear factor of kappa light polypeptide gene enhancer in B-cells inhibitor, alpha; BCL2/adenovirus E1B 19 kDa interacting protein 3; integrin, beta 3 (platelet glycoprotein IIIa, antigen CD61); dual specificity phosphatase 10; cell cycle control protein SDP35; plexin C1; microphthalmia-associated transcription factor; calpain small subunit 2; hypothetical protein DKFZp434L142; MEGF 10 protein; EphA2; jagged 1 (Alagille syndrome); hemicentin; low density lipoprotein receptor (heparin-binding epidermal growth factor-like growth factor); tyrosinase-related protein 1; tyrosinase (oculocutaneous albinism IA); dopachrome tautomerase (dopachrome delta-isomerase, tyrosine-related protein 2); laminin, beta 3; MAX dimerization protein 1; CDK4-binding protein p34SEI1; Homo sapiens cDNA FLJ42435 fis, clone BLADE2006849; growth arrest and DNA-damage-inducible, beta; cycline-dependent kinase inhibitor 2B (p15, inhibits CDK4); Diphtheria toxin receptor (heparin-binding epidermal growth factor-like growth factor); syntaxin binding protein 6 (amisyn); transport-secretion protein 2.2; Arg/Abl-interacting protein ArgBP2; hypothetical protein DJ667H12.2; and Homo sapiens cDNA FLJ37284 fis, clone RAMY2013590.

The above-mentioned and other features of this invention and the manner of obtaining and using them will become more apparent, and will be best understood, by reference to the following description, taken in conjunction with the accompanying drawings. The drawings depict only typical embodiments of the invention and do not therefore limit its scope.

BRIEF DESCRIPTION OF THE FIGURES

FIG. 4. (A) shows representative images of SC144 treated mice. (B) Comparison of the tumor size of SC144 treated (4 mg/kg) and control. (C) Tumors incised from mice shown in panel B.

FIG. 11 shows bioinformatic analysis of genes by molecular function using Genetrix™ tools.

FIG. 12 shows a list of genes derived from InterPro classification tools implemented in Genetrix™.

FIG. 13 shows subset classification of common genes identified between SC144 and etoposide.

FIG. 14 shows subset classification of genes in common among SC144, mitoxantrone, and camptothecin.

DETAILED DESCRIPTION OF THE INVENTION

Figure 1:
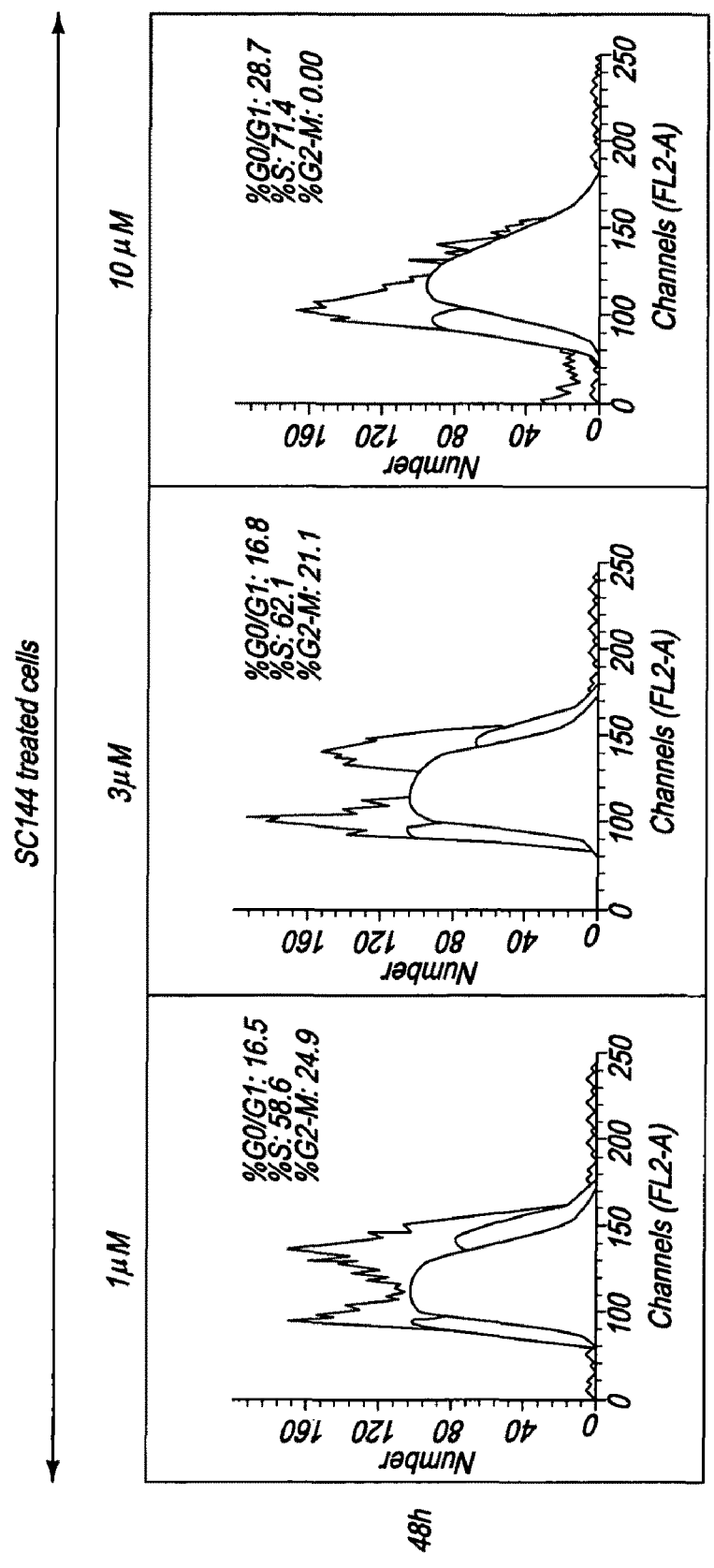
FIG. 1 illustrates flow cytometric analysis of the cell cycle profile of MDA-MB-435 cells treated with SC144. Cells were exposed for 16 h, 24 h and 48 h to SC144, stained with propidium iodide (PI) and analyzed for perturbation in the cell cycle.
Figure 1:
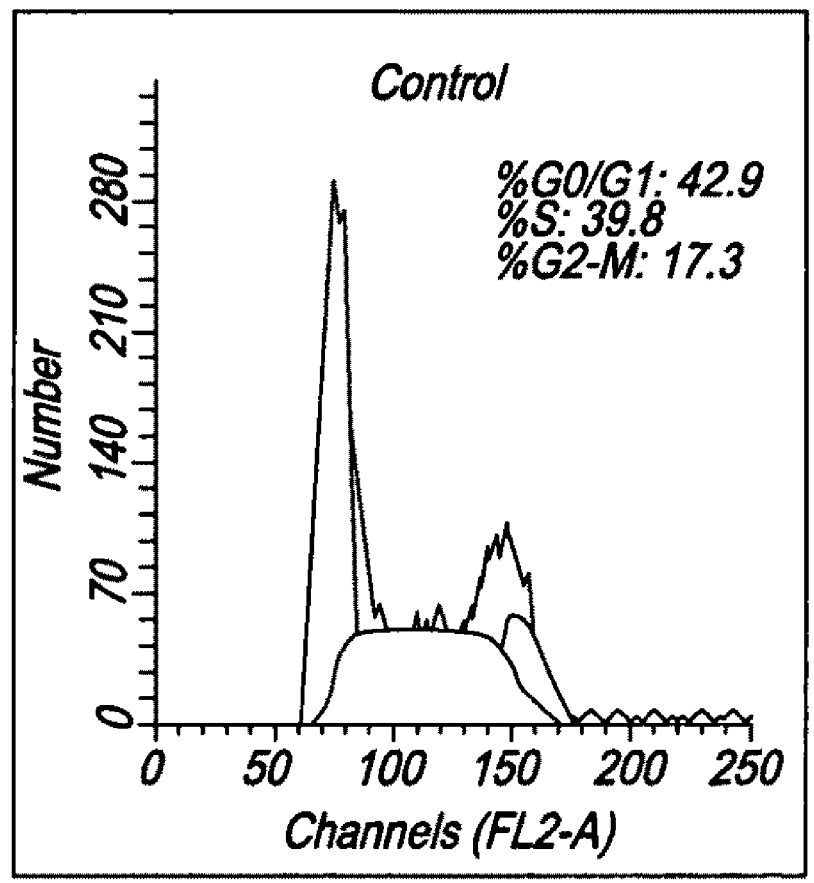

A series of compounds were designed based on three-dimensional anti-tumor structural modeling (specific for inhibition of DNA processing enzymes) integrated with predictive pharmacokinetic (PK) simulations. Several of the compounds showed remarkable cytotoxicity patterns against a panel of human cancer cell lines. A series of 200 compounds were tested against several drug-resistant cancer cell lines. SC144 was selected as a lead molecule based on potency and drug like properties. The compound exhibits in vivo efficacy against breast cancer xenografts in nude mice with no apparent toxicity. The activity of this compound was independent of the status of the hormone receptor (HR), p53, pRb, p21 or p16. Moreover, SC144 blocked cells in S-phase and induced apoptosis in a cisplatin resistant ovarian cancer cell line (HEY) with activity comparable to that of camptothecin. Considering the cytotoxicity profile displayed by this compound in a variety of in vitro models, as well as its effects on cell cycle regulation and apoptosis, SC144 appears to represent a novel and promising candidate for the treatment of cancer and disorders associated with angiogenesis function.

Compounds

A compound of the invention has one of the following formulas:

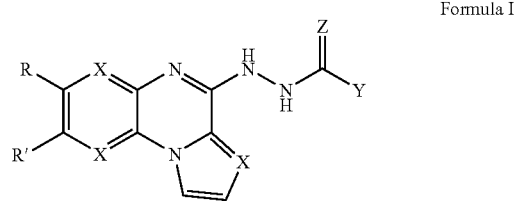

Formula I wherein X=CH or N; Z=O or S; R=alkyl, halogen, acetyl, O-alkyl, or N-alkyl; R'=alkyl, halogen, acetyl, O-alkyl, or N-alkyl; and Y=alkyl, heterocyclic aromatic, aliphatic, sugar, or lipid;

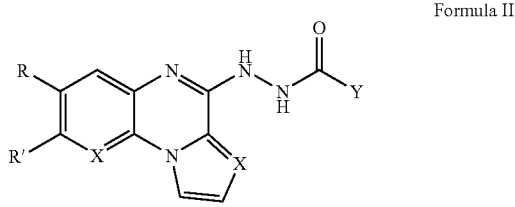

Formula II wherein R is H, alkyl, or halogen; R' is H, alkyl, or halogen; X is CH or N; and Y comprises a homocyclic or heterocyclic ring, wherein Y is 2-pyrazinyl or 2-, 3-, 4-pyridinyl when R is H, R' is H, X is CH, and Y is pyrazinyl or pyridinyl;

Formula III

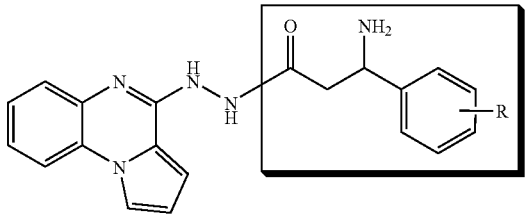

wherein R=o-Cl, p-Cl, p-F, p-CN, p-OMe, or p-CF$_3$;

Formula IV

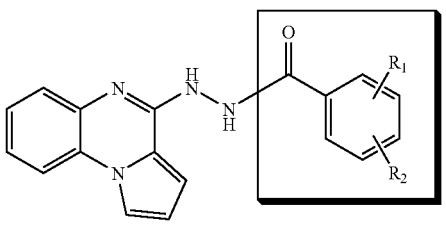

wherein R$_1$=3-NH$_2$, R$_2$=5-CF$_3$; R$_1$=5-NH$_2$, R$_2$=2-NO$_2$; R$_1$=4-NH$_2$, R$_2$=3-NO$_2$; R$_1$=2-NH$_2$, R$_2$=5-OH; R$_1$=4-NH$_2$, R$_2$=H; R$_1$=R$_2$=H; or R$_1$=2—NH$_2$, R$_2$=H;

Formula V

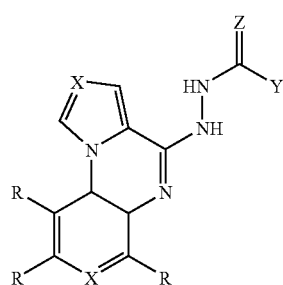

wherein X=CH or N; Z=O or S; R=alkyl, halogen, acetyl, O-alkyl, or N-alkyl; and Y=alkyl, heterocyclic aromatic, aliphatic, sugar, or lipid;

Formula VI

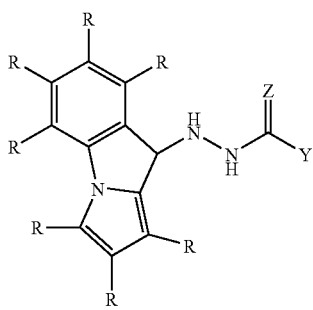

wherein Z=O or S; R=alkyl, halogen, acetyl, O-alkyl, or N-alkyl; and Y=alkyl, heterocyclic aromatic, aliphatic, sugar, or lipid; or Formula VII

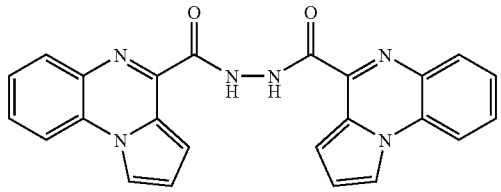

A "homocyclic ring" refers to a closed ring of atoms of the same kind especially carbon atoms; a "heterocyclic ring" refers to a closed ring of atoms of which at least one is not a carbon atom. An "Aromatic" group contains one or more benzene rings. Sugars refer to mono, di, and tri-saccharides and lipid refers to long chain aliphatic compound with or without a hydrophilic head group.

A compound of the invention may include both substituted and unsubstituted moieties. The term "substituted" refers to moieties having one, two, three or more substituents, which may be the same or different, each replacing a hydrogen atom. Examples of substituents include, but are not limited to, alkyl, hydroxyl, protected hydroxyl, amino, protected amino, carboxy, protected carboxy, cyano, alkoxy, and nitro. The term "unsubstituted" refers to a moiety having each atom hydrogenated such that the valency of each atom is filled. An reactive moiety is "protected" when it is temporarily and chemically transformed such that it does not react under conditions where the non-protected moiety reacts. For example, trimethylsilylation is a typical transformation used to protect reactive functional groups such as hydroxyl or amino groups from their reaction with growing anionic species in anionic polymerization.

Protected forms of the compounds are included within the scope of the invention. In general, the species of protecting group is not critical, provided that it is stable to the conditions of any subsequent reactions on other positions of the compound and can be removed at the appropriate point without adversely affecting the remainder of the molecule. In addition, one protecting group may be substituted for another after substantive synthetic transformations are complete. Examples and conditions for the attachment and removal of various protecting groups are found in Greene, Protective Groups in Organic Chemistry, 1st ed., 1981, and 2nd ed., 1991. In addition, salts of the compounds are within the scope of the invention. For example, a salt can be formed between a positively charged amino substituent and a negatively charged counterion.

Compounds of the invention may be prepared, e.g., according to the schemes described below.

The synthesis of SC141-SC144, SC148, and SC153-158 can be accomplished starting from the appropriate 4-chloropyrrolo[1,2-α]quinoxaline 13a-c (Nagarajan et al. (1972) Indian J. Chem. 10:344-350 and Guillon et al. (2004) J. Med. Chem. 17:1997-2009) or 6-chloroimidazo[1,2-α]pyrido[3,2-e]pyrazine 13d (Campiani et al. (1997) J. Med. Chem. 40:3670-3678) and hydrazine monohydrate to give essentially pure 4-hydrazinopyrrolo[1,2-α]quinoxalines 14a-c and 6-hydrazinoimidazo[1,2-α]pyrido[3,2-e]pyrazine 14d, respectively (Scheme 1). The subsequent N-acylation step can be performed in different experimental conditions: the SC141 and SC142 can be obtained by reaction of compound 14a with pyrrole-2-carboxylic acid chloride and nicotinoyl chloride hydrochloride, respectively; while SC143, SC144 and SC148 can be obtained by reaction of derivatives 14b-d with commercial 2-pyrazinecarboxylic acid by use of 2,2'-dipyrildisulphide and triphenylphosphine as condensing reagents (Di Fabio et al. (1993) Tetrahedron 43:229-2306). The condensation between hydrazine derivative 14a and an appropriate indolecarboxylic acid by a 1-[3-(dimethylamino)propyl]-3-ethylcarbodiimide hydrochloride (EDC)/4-(dimethylamino)pyridine (DMAP) system gives compounds SC155-158; N—BOC-derivatives of compounds SC153 and SC154 can be synthesized starting from compound 14a and N—BOC-thiazolidine-4-carboxylic acid or N—BOC-β-alanine, respectively, using again EDC/DMAP as a dehydrating system and finally deprotected by means of trifluoroacetic acid (TFA)/anisole.

Scheme 1

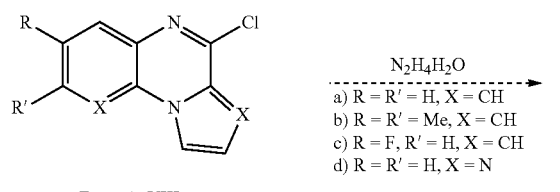

Formula VIII
13a-d

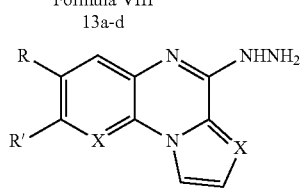

Formula IX
14a-d a) R = R' = H, X = CH
b) R = R' = Me, X = CH
c) R = F, R' = H, X = CH
d) R = R' = H, X = N 1) acylation
2) deprotection
(for SC153-154)

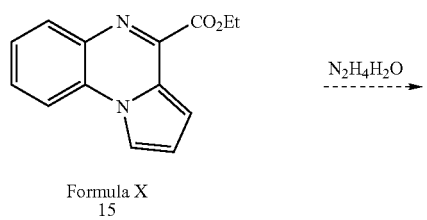

Formula II

SC141-SC144, SC148, and SC153-158

The preparation of bis-derivatives SC147 can be performed by direct reaction of hydrazine monohydrate with two molar equivalents of ethyl pyrrolo[1,2-α]quinoxaline-4-carboxylate 15, in turn obtained after the fashion of Nagarajan et al. ((1972) Indian J. Chem. 10:344-350) (Scheme 2).

Scheme 2

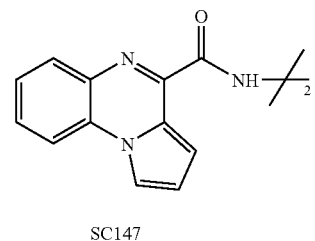

Formula X
15

-continued

SC147

SC160, SC161, SC162, SC163, SC164, and SC165 can be obtained by reaction of 14a with Boc-3-amino-3-(2-chlorophenyl)propionic acid, Boc-3-amino-3-(4-chlorophenyl)propionic acid, Boc-3-amino-3-(4-fluorophenyl)propionic acid, Boc-3-amino-3-(4-cyanophenyl)propionic acid, Boc-3-amino-3-(4-methoxyphenyl)propionic acid, and Boc-3-amino-3-(4-trifluoromethylphenyl)propionic acid in the presence of EDC/DMAP followed by TFA and anisole, respectively (Scheme 3).

Scheme 3

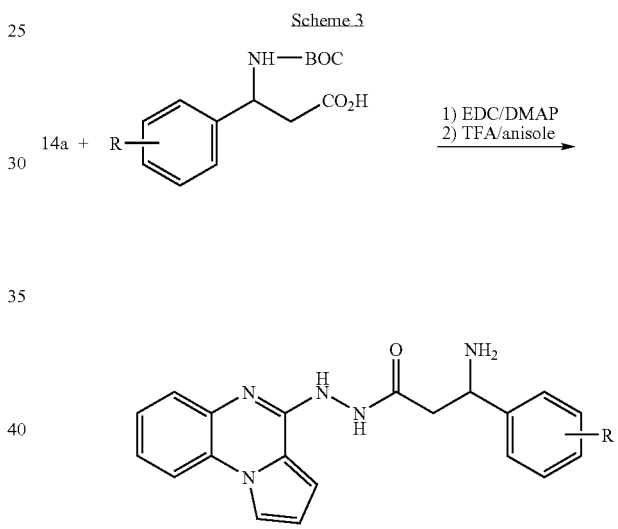

1) EDC/DMAP
2) TFA/anisole

| Compd | R |
|-------|------|
| SC160 | 2-Cl |
| SC161 | 4-Cl |
| SC162 | 4-F |
| SC163 | 4-CN |
| SC164 | 4-OCH3 |
| SC165 | 4-CF3 |

SC166, SC167, SC168, SC169, SC170, SC171, and SC172 can be obtained by reaction of 14a with corresponding acid (15a-g) shown in Scheme 4 in the presence of EDC/DMAP followed by TFA and anisole, respectively (Scheme 4).

Scheme 4

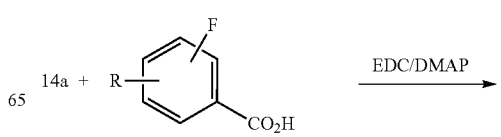

EDC/DMAP

-continued

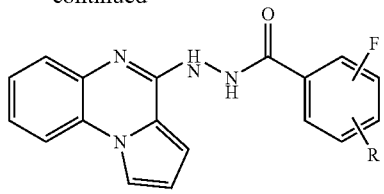

| Compd | R |
|---|---|
| SC166 | 2-F, R = H |
| SC167 | 2-F, R = 4-OH |
| SC168 | 3-F, R = H |
| SC169 | 3-F, R = 4-CF$_3$ |
| SC170 | 4-F, R = H |
| SC171 | 4-F, R = 2-OH |
| SC172 | 3-F, R = NO$_2$ |

SC173 can be obtained by reaction of 14a with 2-quinoxalinecarboxylic acid, dichloromethane, triphenylphosphine, and 2,2'-dipyridyl disulfide; SC174 can be obtained by reaction of 14a with pyrrolo[1,2-α]quinoxaline-4-carboxylic acid, dichloromethane, triphenylphosphine, and 2,2'-dipyridyl disulfide.

SC175 can be obtained by reaction of nicotinoyl chloride hydrochloride with 9-hydrazino-9H-pyrrolo[1,2-α]indole and pyridine; SC176 can be obtained by reaction of 2-pyrazine carboxylic acid with 9-hydrazino-9H-pyrrolo[1,2-α]indole (Scheme 5).

Scheme 5

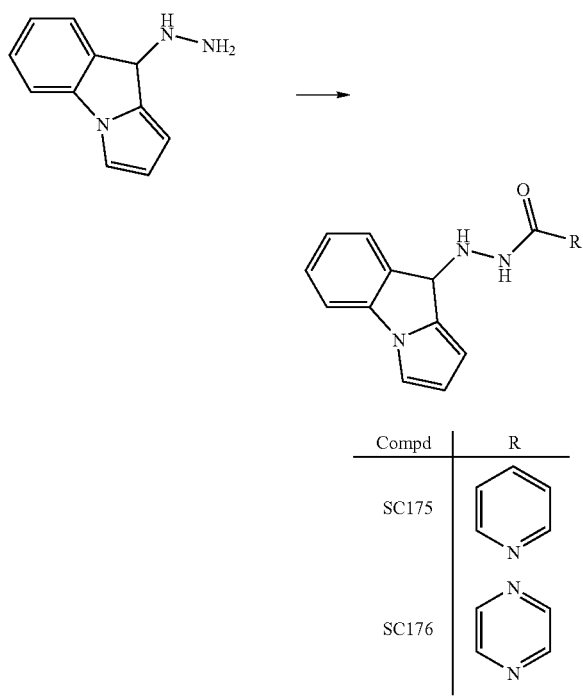

| Compd | R |
|---|---|
| SC175 | pyridyl |
| SC176 | pyrazinyl |

Compositions

The compounds of the invention can be incorporated into pharmaceutical compositions. Such compositions typically include the compounds and pharmaceutically acceptable carriers. "Pharmaceutically acceptable carriers" include solvents, dispersion media, coatings, antibacterial and antifungal agents, isotonic and absorption delaying agents, and the like, compatible with pharmaceutical administration. Other active compounds (e.g., taxol, doxorubicin, or 5-FU) can also be incorporated into the compositions.

A pharmaceutical composition is formulated to be compatible with its intended route of administration. See, e.g., U.S. Pat. No. 6,756,196. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the compounds in the required amounts in an appropriate solvent with one or a combination of ingredients enumerated above, as required, followed by filtered sterilization. Generally, dispersions are prepared by incorporating the compounds into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the compounds can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the compounds are prepared with carriers that will protect the compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. "Dosage unit form," as used herein, refers to physically discrete units suited as unitary dosages for the subject to be treated; each unit containing a predetermined quantity of active compound calculated to produce the desired therapeutic effect in association with the required pharmaceutical carrier.

Pharmaceutical compositions can be included in a container, pack, or dispenser together with instructions for administration to form packaged products. For example, a packaged product may comprise a container; an effective amount of a compound of the invention; and an insert associated with the container, indicating administering the compound for treating cancer or a disorder associated with angiogenesis function.

In another example, an effective amount of a compound of formula XI or XII,

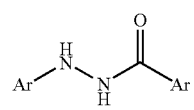

Formula XI

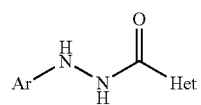

Formula XII wherein Ar comprises an aromatic ring and Het comprises a heterocyclic ring, may be packaged in a container with an insert. The insert is associated with the container and contains instructions for administration of the compound for treating non-small cell lung cancer, CNS cancer, ovarian cancer, breast cancer, renal cancer, prostate cancer, age-related macular degeneration, macular dystrophy, or diabetes.

Alternatively, an effective amount of a compound of Formula II,

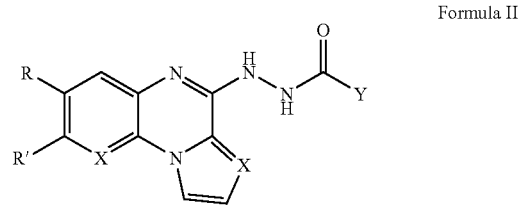

Formula II wherein R is H, alkyl, or halogen; R' is H, alkyl, or halogen; X is CH or N; and Y comprises a homocyclic or heterocyclic ring, may be packaged in a container with an insert. The insert is associated with the container and contains instructions for administration of the compound for treating cancer or a disorder associated with angiogenesis function.

A packaged product may further comprise an effective amount of one or more other agents for treating cancer or a disorder associated with angiogenesis function, e.g., taxol, doxorubicin, or 5-FU.

Uses

Method of Treatment

The present invention provides for both prophylactic and therapeutic methods of treating a subject in need thereof an effective amount of a compound or composition described above.

"Subject," as used herein, refers to a human or animal, including all vertebrates, e.g., mammals, such as primates (particularly higher primates), sheep, dog, rodents (e.g., mouse or rat), guinea pig, goat, pig, cat, rabbit, cow; and non-mammals, such as chicken, amphibians, reptiles, etc. In a preferred embodiment, the subject is a human. In another embodiment, the subject is an experimental animal or animal suitable as a disease model.

A subject to be treated may be identified, e.g., using diagnostic methods known in the art, as being suffering from or at risk for developing cancer or a disorder associated angiogenesis function, i.e., blood vessel formation, which usually accompanies the growth of malignant tissue. The subject may be identified in the judgment of a subject or a health care professional, and can be subjective (e.g., opinion) or objective (e.g., measurable by a test or diagnostic method). Examples of cancer include leukemia, non-small cell lung cancer, colon cancer, CNS cancer, melanoma, ovarian cancer, breast cancer, renal cancer, or prostate cancer; examples of disorders associated with angiogenesis function include age-related macular degeneration, macular dystrophy, or diabetes.

As used herein, the term "treatment" is defined as the application or administration of a therapeutic agent to a subject, or application or administration of a therapeutic agent to an isolated tissue or cell line from a subject, who has a disease, a symptom of disease or a predisposition toward a disease, with the purpose to cure, heal, alleviate, relieve, alter, remedy, ameliorate, improve or affect the disease, the symptoms of disease or the predisposition toward disease.

An "effective amount" is an amount of the therapeutic agent that is capable of producing a medically desirable result as delineated herein in a treated subject. The medically desirable result may be objective (i.e., measurable by some test or marker) or subjective (i.e., subject gives an indication of or feels an effect).

Toxicity and therapeutic efficacy of the compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of the compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of a compound which achieves a half-maximal inhibition of symptoms) as determined in cell culture. Such information can be used to more accurately determine useful doses in humans. Levels in plasma may be measured, for example, by high performance liquid chromatography.

A therapeutically effective amount of the compounds (i.e., an effective dosage) may range from, e.g., about 1 microgram per kilogram to about 500 milligrams per kilogram, about 100 micrograms per kilogram to about 5 milligrams per kilogram, or about 1 microgram per kilogram to about 50 micrograms per kilogram. The compounds can be administered, e.g., one time per week for between about 1 to 10 weeks, preferably between 2 to 8 weeks, more preferably between about 3 to 7 weeks, and even more preferably for about 4, 5, or 6 weeks. It is furthermore understood that appropriate doses of a compound depend upon the potency of the compound. When one or more of these compounds is to be administered to a subject (e.g., an animal or a human), a physician, veterinarian, or researcher may, for example, prescribe a relatively low dose at first, subsequently increasing the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, any drug combination, the severity of the disease or disorder, previous treatments, and other diseases present. Moreover, treatment of a subject with a therapeutically effective amount of the compounds can include a single treatment or, preferably, can include a series of treatments.

The treatment may further include administering to the subject an effective amount of one or more other agents for treating cancer or a disorder associated with angiogenesis function, e.g., taxol, doxorubicin, or 5-FU. When multiple therapeutic agents are used, the agents may be administered, simultaneously or sequentially, as mixed or individual dosages.

Method of Monitoring Treatment Using PET Technology

Miniaturized, high-resolution PET scanners employing novel detector technology have been designed specifically for small animal imaging (Holdsworth and Thornton (2002) Trends Biotechnol. 20:S34-39 and Lewis et al. (2002) Eur. J. Cancer 38:2173-2188). This approach allows the rapid testing of drug effects in human tumor xenografts implanted into mice in order to optimize drug PK and dose regimens prior to testing in humans. Such in vivo assessment can predict success of drug candidates, thus filtering potential clinical candidates earlier in the drug discovery pipeline. As applied to drug discovery and development, information obtainable via functional PET imaging can be divided into four categories: (1) the absorption, distribution, metabolism and elimination of the labeled drug candidate; (2) the delivery of a drug to a specific target of interest (e.g., tumor); (3) the interaction of a drug or drug candidate with the desired molecular target (e.g., an enzyme or cell surface receptor); and (4) determination of desirable PD effects (e.g., cell killing and cell cycle arrest) or undesirable side effects. Noninvasive PET imaging techniques can enable more accurate titration of therapeutic dose and, using a labeled form of the drug, more rapid characterization of PK and PD, linking in vivo affinity with efficacy. This will inevitably improve data quality, reduce costs and animal numbers used and, most importantly, decrease the work-up time for new compounds.

PET imaging with the glucose analog [$^{18}$F]fluorodeoxyglucose ([$^{18}$F]FDG) has been used extensively in human patients to visualize primary cancers with a high degree of accuracy and to quantify cancer response to antineoplastic therapies; an example of this in breast cancer can be found in references (Bellon et al. (2004) Am. J. Clin. Oncol. 27:407-410 and Eubank and Mankoff (2004) Semin. Nucl. Med. 34:224-240). Early assessment of in vivo efficacy of new drugs in mice by PET could greatly aid selection of the right drug for future clinical studies. The generally high rate of glycolysis by tumor cells can be quantitated by PET/[$^{18}$F] FDG imaging. FDG is phosphorylated by hexokinase, yielding negatively charged FDG-6-phosphate, which is effectively trapped in the cell. Increased tumor uptake of FDG as measured by PET is highly correlated with viable tumor density (i.e., viable cell number per unit tissue volume). Because FDG uptake is representative of tumor cell viability (Higashi et al. (1993) J. Nucl. Med. 34:773-779) reduction in FGD uptake with effective tumor therapy reflects killing of tumor cells. Evaluation of tumor response in experimental animal models is of paramount importance in drug development, and FDG PET is an ideal tool for this purpose. In fact, a number of clinical trials have already shown that quantification of the changes in tumor [$^{18}$F]-FDG uptake may provide an early, sensitive, pharmacodynamic marker of the tumoricidal effect of anticancer drugs. Changes in FDG PET images during chemotherapy are predictive of response in patients with a variety of cancers such as breast carcinoma (Avril et al.

(2000) J. Clin. Oncol. 18:3495-3502), lung (Higashi et al. (2002) J. Nucl. Med. 43:39-45), head and neck carcinoma (Halfpenny et al. (2002) Br. J. Cancer 86:512-516), and lymphoma (Lowe and Wiseman (2002) J. Nucl. Med. 43:1028-1030) (for reviews, see Czernin and Phelps (2002) Annu. Rev. Med. 53:89-112, Cohade and Wahl (2002) Cancer J. 8:119-134, and Nabi and Zubeldia (2002) J. Nucl. Med. Technol. 30:3-9; quiz 10-11). These studies demonstrate that PET can identify clinical response to treatment at a much earlier stage in the therapeutic regimen than is possible using conventional procedures based on change in tumor size.

An important characteristic of highly proliferating cells is their remarkable rate of DNA synthesis. PET probes that are incorporated into the DNA synthetic pathway are ideal agents with which to measure tumor growth rate and the impact of treatment on tumor cell division. The prototype agent in this class is thymidine. Unfortunately, the utility of thymidine is limited due to its rapid catabolism in vivo (Conti et al. (1994) Nucl. Med. Biol. 21:1045-1051). During the past decade several radiolabeled analogs of thymidine that are resistant to enzymatic degradation and are incorporated into DNA with high specificity and affinity have been identified (see, for example, Czernin and Phelps (2002) Annu. Rev. Med. 53:89-112, Cohade and Wahl (2002) Cancer J. 8:119-134). One such radiotracer, 2'-fluoro-5-methyl-1-β-D-arabinofuranosyluracil (FMAU) labeled with C-11 (20 min half life) has shown promise for tumor imaging with PET (Conti et al. (1995) Nucl. Med. Biol. 22:783-789, Bading et al. (2000) Nucl. Med. Biol. 27:361-368, and Bading et al. (2004) Nucl. Med. Biol. 31:407-418). Following cellular uptake, FMAU is phosphorylated by thymidine kinase and incorporated into DNA.

Accordingly, the invention provides a method of monitoring treatment of a subject. The method involves administering to a subject having cancer cells or cells associated with an angiogenesis function disorder a compound described above and measuring the survival of the cells, the growth of the cells, or a combination thereof using PET imaging. The subject may be suffering from leukemia, non-small cell lung cancer, colon cancer, CNS cancer, melanoma, ovarian cancer, breast cancer, renal cancer, or prostate cancer. The subject may be an animal, e.g., a mouse, and the cells may be xenografted human cells. Preferably, the subject is a human.

Method of Profiling Gene Expression

Gene expression patterns in response to drug treatment are strong indications of the mechanism of action, mechanism of resistance and cellular pathways for the drug. Profiling of gene expression, e.g., by means of DNA microarray technology, is useful for identifying and validating drug targets, and for monitoring drug treatment.

Accordingly, the invention provides a method of profiling gene expression by contacting a test cell with a compound described above and profiling gene expression in the test cell. In particular, the test cell may be a cancer cell or a cell associated with an angiogenesis function disorder, e.g., a leukemia cell, non-small cell lung cancer cell, colon cancer cell, CNS cancer cell, melanoma cell, ovarian cancer cell, breast cancer cell, renal cancer cell, prostate cancer cell, or a cell associated with age-related macular degeneration, macular dystrophy, or diabetes. Gene expression in the test cell may be compared with that in a control cell, e.g., a cell not contacted with the compound, a cell contacted with another compound with known action, or a cell resistant to the compound. Such comparison provides useful information for understanding the action of the compound.

Gene expression can be determined at mRNA and protein levels. The presence, level, or absence of a protein or nucleic acid in a biological sample can be evaluated by obtaining a biological sample from a test subject and contacting the biological sample with an agent capable of detecting the protein or nucleic acid (e.g., mRNA, genomic DNA) that encodes the protein such that the presence of the protein or nucleic acid is detected in the biological sample. The term "biological sample" includes tissues, cells and biological fluids isolated from a subject, as well as tissues, cells and fluids present within a subject. The level of expression of a gene can be measured in a number of ways, including, but not limited to: measuring the mRNA transcribed from the gene, measuring the amount of protein encoded by the gene, or measuring the activity of the protein encoded by the gene.

The level of mRNA transcribed from the gene in a cell can be determined both by in situ and by in vitro formats. The isolated mRNA can be used in hybridization or amplification assays that include, but are not limited to, Southern or Northern analyses, polymerase chain reaction analyses and probe arrays. One preferred diagnostic method for detection of the mRNA level involves contacting the isolated mRNA with a nucleic acid molecule (probe) that can hybridize to the mRNA transcribed from the gene being detected. The probe can be disposed on an address of an array.

In one format, mRNA (or cDNA) is immobilized on a surface and contacted with the probes, for example, by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array. A skilled artisan can adapt known mRNA detection methods for use in detecting the level of mRNA transcribed from the gene.

The level of mRNA in a sample can be evaluated with nucleic acid amplification, e.g., by RT-PCR (U.S. Pat. No. 4,683,202), ligase chain reaction (Barany (1991) Proc. Natl. Acad. Sci. USA 88:189-193), self sustained sequence replication (Guatelli et al. (1990) Proc. Natl. Acad. Sci. USA 87:1874-1878), transcriptional amplification system (Kwoh et al. (1989) Proc. Natl. Acad. Sci. USA 86:1173-1177), Q-Beta Replicase (Lizardi et al. (1988) Bio/Technology 6:1197), rolling circle replication (U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA transcribed from the gene being analyzed.

A variety of methods can be used to determine the level of protein encoded by the gene. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')$_2$) can be used. The term "labeled," with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance.

The detection methods can be used to detect a protein in a biological sample in vitro as well as in vivo. In vitro techniques for detection of a protein include enzyme linked immunosorbent assays (ELISAs), immunoprecipitations, immunofluorescence, enzyme immunoassay (EIA), radioimmunoassay (RIA), and Western blot analysis. In vivo techniques for detection of a protein include introducing into a subject a labeled antibody. For example, the antibody can be labeled with a radioactive marker whose presence and location in a subject can be detected by standard imaging techniques. In another embodiment, the sample is labeled, e.g., biotinylated and then contacted to the antibody, e.g., an antibody positioned on an antibody array. The sample can be detected, e.g., with avidin coupled to a fluorescent label.

It is now well established that DNA microarray technology allows simultaneous quantification of the expression of thousands of genes. This methodology is now robust, reproducible, and highly efficient. It can be used to evaluate cellular pathways and validate drug targets (see, for example, Clarke et al. (2001) Biochem. Pharmacol. 62:1311-1336, Onyango (2004) Curr. Cancer Drug Targets 4:111-124, and Weinstein (2002) Curr. Opin. Pharmacol. 2:361-365).

Clustering of compounds into presumed mechanistic groupings based on the similarity in their growth inhibition profiles across the NCI 60 human cancer cell-lines was first realized by Paull et al. ((1989) J. Natl. Cancer Inst. 81:1088-1092). They developed a computer program called "COMPARE" which is based on a pattern recognition algorithm that assesses the degree of similarity of compounds based on their cytotoxicity profiles. Some of the compounds were classified according to their published and widely accepted molecular targets. Recently, Dr. John Weinstein and his colleagues at NCI have created a software package called "DISCOVERY" to compare the gene expression analysis of 60 cell lines using a cDNA chip containing 1,200 genes (Weinstein et al. (1997) Science 275:343-349). A correlation between gene expression patterns and the cytotoxic profiles against 60 cell lines in response to a particular compound could be determined (Scherf et al. (2000) Nat. Genet. 24:236-244). Using this methodology, it is possible to identify targets or pathways for these compounds. DISCOVERY then allows the identification of genes common to the pathways by correlative gene expression. This publicly available software allows comparison of compounds against a database of 5000 compounds in the NCI 60 human cancer cell-lines (see the NCI web site at discover.nci.nih.gov).

Genes identified through profiling as responsive to the treatment of a compound may be used as therapeutic markers. These markers can in turn be used to monitor treatment of a subject with the compound. For example, genes responsive to SC144 include small proline-rich protein 1A; GTP binding protein overexpressed in skeletal muscle; interleukin 24; sestrin 2; hypothetical protein MGC4504; cyclin-dependent kinase inhibitor 1A (p21); early growth response 1; ATPase, H+ transporting, lysosomal 38 kDa, V0 subunit d isoform 2; AXIN1 up-regulated 1; dual specificity phosphatase 5; superoxide dismutase 2, mitochondrial; heparin-binding epidermal growth factor-like growth factor; A disintegrin and metalloproteinase domain 19 (meltrin beta); endothelial PAS domain protein 1; inositol 1,4,5-triphosphate receptor, type 1; tissue factor pathway inhibitor (lipoprotein-associated coagulation inhibitor); fibrinogen, gamma polypeptide; RAB20, member RAS oncogene family; protein kinase, AMP-activated, gamma 2 non-catalytic subunit; oncostatin M receptor; cathepsin B; nuclear factor of kappa light polypeptide gene enhancer in B-cells inhibitor, alpha; BCL2/adenovirus E1B 19 kDa interacting protein 3; integrin, beta 3 (platelet glycoprotein IIIa, antigen CD61); dual specificity phosphatase 10; cell cycle control protein SDP35; plexin C1; microphthalmia-associated transcription factor; calpain small subunit 2; hypothetical protein DKFZp434L142; MEGF 10 protein; EphA2; jagged 1 (Alagille syndrome); hemicentin; low density lipoprotein receptor (heparin-binding epidermal growth factor-like growth factor); tyrosinase-related protein 1; tyrosinase (oculocutaneous albinism IA); dopachrome tautomerase (dopachrome delta-isomerase, tyrosine-related protein 2); laminin, beta 3; MAX dimerization protein 1; CDK4-binding protein p34SEI1; Homo sapiens cDNA FLJ42435 fis, clone BLADE2006849; growth arrest and DNA-damage-inducible, beta; cycline-dependent kinase inhibitor 2B (p15, inhibits CDK4); Diphtheria toxin receptor (heparin-binding epidermal growth factor-like growth factor); syntaxin binding protein 6 (amisyn); transport-secretion protein 2.2; Arg/Abl-interacting protein ArgBP2; hypothetical protein DJ667H12.2; and Homo sapiens cDNA FLJ37284 fis, clone RAMY2013590. One or more of these genes may be used as markers for monitoring treatment of a subject with SC144, e.g., determining the efficacy of the compound.

Method of Modulating Gene Expression

Another aspect of the invention pertains to methods of modulating gene expression or activity for therapeutic purposes. Accordingly, the modulatory method of the invention involves contacting a cell with a compound described above that modulates expression of one or more of the genes associated with the cell. Examples of the genes include small proline-rich protein 1A; GTP binding protein overexpressed in skeletal muscle; interleukin 24; sestrin 2; hypothetical protein MGC4504; cyclin-dependent kinase inhibitor 1A (p21); early growth response 1; ATPase, H+ transporting, lysosomal 38 kDa, V0 subunit d isoform 2; AXIN1 up-regulated 1; dual specificity phosphatase 5; superoxide dismutase 2, mitochondrial; heparin-binding epidermal growth factor-like growth factor; A disintegrin and metalloproteinase domain 19 (meltrin beta); endothelial PAS domain protein 1; inositol 1,4,5-triphosphate receptor, type 1; tissue factor pathway inhibitor (lipoprotein-associated coagulation inhibitor); fibrinogen, gamma polypeptide; RAB20, member RAS oncogene family; protein kinase, AMP-activated, gamma 2 non-catalytic subunit; oncostatin M receptor; cathepsin B; nuclear factor of kappa light polypeptide gene enhancer in B-cells inhibitor, alpha; BCL2/adenovirus E1B 19 kDa interacting protein 3; integrin, beta 3 (platelet glycoprotein IIIa, antigen CD61); dual specificity phosphatase 10; cell cycle control protein SDP35; plexin C1; microphthalmia-associated transcription factor; calpain small subunit 2; hypothetical protein DKFZp434L142; MEGF 10 protein; EphA2; jagged 1 (Alagille syndrome); hemicentin; low density lipoprotein receptor (heparin-binding epidermal growth factor-like growth factor); tyrosinase-related protein 1; tyrosinase (oculocutaneous albinism IA); dopachrome tautomerase (dopachrome delta-isomerase, tyrosine-related protein 2); laminin, beta 3; MAX dimerization protein 1; CDK4-binding protein p34SEI1; Homo sapiens cDNA FLJ42435 fis, clone BLADE2006849; growth arrest and DNA-damage-inducible, beta; cycline-dependent kinase inhibitor 2B (p15, inhibits CDK4); Diphtheria toxin receptor (heparin-binding epidermal growth factor-like growth factor); syntaxin binding protein 6 (amisyn); transport-secretion protein 2.2; Arg/Abl-interacting protein ArgBP2; hypothetical protein DJ667H12.2; and Homo sapiens cDNA FLJ37284 fis, clone RAMY2013590.

In one embodiment, the compound stimulates expression of one or more of the genes in the cell. For example, SC144 stimulates expression of small proline-rich protein 1A; GTP binding protein overexpressed in skeletal muscle; interleukin 24; sestrin 2; hypothetical protein MGC4504; cyclin-dependent kinase inhibitor 1A (p21); early growth response 1; ATPase, H+ transporting, lysosomal 38 kDa, V0 subunit d isoform 2; AXIN1 up-regulated 1; dual specificity phosphatase 5; superoxide dismutase 2, mitochondrial; heparin-binding epidermal growth factor-like growth factor; A disintegrin and metalloproteinase domain 19 (meltrin beta); endothelial PAS domain protein 1; inositol 1,4,5-triphosphate receptor, type 1; tissue factor pathway inhibitor (lipoprotein-associated coagulation inhibitor); fibrinogen, gamma polypeptide; RAB20, member RAS oncogene family; protein kinase, AMP-activated, gamma 2 non-catalytic subunit; oncostatin M receptor; cathepsin B; nuclear factor of kappa light polypeptide gene enhancer in B-cells inhibitor, alpha; BCL2/adenovirus E1B 19 kDa interacting protein 3; integrin, beta 3 (platelet glycoprotein IIIa, antigen CD61); and dual specificity phosphatase 10. In another embodiment, the compound inhibits expression of one or more of the genes in the cell. For example, SC144 inhibits expression of cell cycle control protein SDP35, plexin C1, microphthalmia-associated transcription factor, calpain small subunit 2, hypothetical protein DKFZp434L142.

These modulatory methods can be performed in vitro, e.g., by culturing the cell with the compound. For example, the cell may be a cancer cell (e.g., a leukemia cell, non-small cell lung cancer cell, colon cancer cell, CNS cancer cell, melanoma cell, ovarian cancer cell, breast cancer cell, renal cancer cell, prostate cancer cell) or a cell associated with an angiogenesis function disorder (e.g., a cell associated with age-related macular degeneration, macular dystrophy, or diabetes). Alternatively, the modulatory methods can be performed in vivo, e.g., by administering the compound to a subject such as a subject suffering from or at risk for developing cancer or a disorder associated with angiogenesis function. As such, the present invention provides methods of treating a subject afflicted with a disease or disorder characterized by aberrant or unwanted expression of one or more of the genes. Stimulation of gene expression is desirable in situations in which the gene is abnormally downregulated and/or in which increased gene expression is likely to have a beneficial effect. Likewise, inhibition of gene expression is desirable in situations in which gene expression is abnormally upregulated and/or in which decreased gene expression is likely to have a beneficial effect.

The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation.

EXAMPLES

Chemistry.

All reactions were carried out under a nitrogen atmosphere. Progress of the reaction was monitored by TLC on silica gel plates (Merck 60, $F_{254}$, 0.2 mm). Organic solutions were dried over $MgSO_4$; evaporation refers to removal of solvent on a rotary evaporator under reduced pressure. Melting points were measured using a Gallenkamp apparatus and are uncorrected. IR spectra were recorded as thin films on Perkin-Elmer 398 and FT 1600 spectrophotometers. $^1H$ NMR spectra were recorded on a Brüker 300-MHz spectrometer with TMS as an internal standard: chemical shifts are expressed in δ values (ppm) and coupling constants (J) in Hz. Mass spectral data were determined by direct insertion at 70 eV with a VG70 spectrometer. Merck silica gel (Kieselgel 60/230-400 mesh) was used for flash chromatography columns. Elemental analyses were performed on a Perkin-Elmer 240C elemental analyzer, and the results are within ±0.4% of the theoretical values. Yields refer to purified products and are not optimized.

General procedure for the preparation of compounds 14a-14d. The preparation of 7-fluoro-4-hydrazinopyrrolo[1,2-α]quinoxaline 14c is reported as a representative example.

A mixture of 7-fluoro-4-chloropyrrolo[1,2-α]quinoxaline 13c (100 mg, 0.45 mmol), hydrazine monohydrate (5 mL), and DMF (2 mL) was heated to 70-80° C. for 1 h. Crushed ice was then added and the mixture was extracted with EtOAc. The organic layer was separated and shaken with water and brine successively. After evaporation of the volatiles, compound 14c was obtained as a solid (84 mg, 86% yield) and used in the subsequent step without further purification. An analytical sample was obtained by crystallization; mp 158° C. (dec.) (dichloromethane/light petroleum); IR (KBr) 3300 $cm^{-1}$; $^1H$ NMR (DMSO-$d_6$) 4.56 (bs, 2H), 6.66 (t, 1H, J=3.2 Hz), 7.03 (m, 2H), 7.18 (dd, 1H, J=10.6, 2.7 Hz), 8.02 (dd, 1H, J=8.9, 5.6 Hz), 8.15 (s, 1H), 8.87 (bs, 1H). Anal. Calcd for $C_{11}H_9FN_4$: C, H, N.

1H-Pyrrole-2-carboxylic acid N'-pyrrolo[1,2-α]quinoxalin-4-yl-hydrazide 1 SC141. A suspension of pyrrole-2-carboxylic acid chloride (58 mg, 0.45 mmol) and triethylamine (1 mL) in dry THF (10 mL) was added portionwise to a stirred solution of compound 14a (90 mg, 0.45 mmol) in dry THF (3 mL). The mixture was stirred overnight at room temperature. The residue obtained after evaporation of the volatiles was partitioned between ethyl acetate and water. The organic layer separated was shaken with brine and dried. Evaporation of the solvent gave compound 1 as a white solid (82 mg, 62% yield); mp 210-212° C. (methanol); IR (KBr) 3255, 1675 $cm^{-1}$;
$^1H$ NMR (DMSO-$d_6$) 6.14 (s, 1H), 6.77 (t, 1H, J=3.1 Hz), 6.99 (s, 1H), 7.13 (d, 1H, J=3.7 Hz), 7.25 (m, 2H), 7.42 (m, 2H), 8.06 (m, 1H), 8.27 (m, 1H), 9.32 (bs, 1H), 10.11 (bs, 1H) 11.58 (bs, 1H). MS (CI) m/z 292 ($MH^+$). Anal. Calcd. for $C_{16}H_{13}N_5O$: C, H, N.

Nicotinic acid N'-pyrrolo[1,2-α]quinoxalin-4-yl-hydrazide 2 (SC142). Solid nicotinoyl chloride hydrochloride (155 mg, 0.90 mmol) was added portionwise to a stirred and ice-cooled solution of 4-hydrazinopyrrolo[1,2-α]quinoxaline 14a (200 mg, 1.01 mmol) in dry pyridine (15 mL). The mixture was stirred overnight at room temperature. After a usual work-up, compound 2 was obtained as a pale yellow solid (122 mg, 40% yield); mp 237° C. (methanol/ethyl acetate); IR (KBr) 3245, 1680 $cm^{-1}$; $^1H$ NMR (DMSO-$d_6$) 6.70 (m, 1H), 7.07 (m, 1H), 7.18 (m, 2H), 7.36 (m, 1H), 7.48 (m, 1H), 7.98 (m, 1H), 8.20 (m, 2H), 8.69 (m, 1H), 9.05 (m, 1H), 10.75 (bs, 1H), 11.80 (bs, 1H). MS (CI) m/z 304 ($MH^+$). Anal. Calcd. for $C_{17}H_{13}N_5O$: C, H, N.

Pyrazine-2-carboxylic acid N'-(7,8-dimethylpyrrolo[1,2-α]quinoxalin-4-yl)-hydrazide 3 (SC143). To a stirred suspension of 2-pyrazinecarboxylic acid (62 mg, 0.50 mmol) in dry dichloromethane (2 mL) were added, portion wise, within 1 h, triphenylphosphine (262 mg, 1.00 mmol) and 2,2'-dipyridyl disulfide (220 mg, 1.00 mmol). When the starting material disappeared (TLC) a solution of 4-hydrazino-7,8-dimethylpyrrolo[1,2-α]quinoxaline 14b (113 mg, 0.50 mmol) in the same solvent (6 mL) was added and the resulting mixture was stirred at room temperature overnight. The solvent was removed and the residue was partitioned between ethyl acetate and water. The organic layer was separated, shaken with brine and dried. The residue left after evaporation of the solvent was purified by flash-chromatography (chloroform: methanol:ammonium hydroxide, 89:10:1) to afford compound 3 as a pale yellow solid (63 mg, 38% yield); mp 116° C. (methanol/ethyl acetate); IR (KBr) 3250, 1675 cm$^{-1}$; $^1$H NMR (DMSO-d$_6$) 3.35 (s, 6H), 6.74 (t, 1H, J=3.8 Hz), 7.31 (d, 1H, J=3.8 Hz), 7.42 (m, 1H), 7.64 (m, 2H), 7.87 (bs, 1H), 8.28 (bs, 1H), 8.71 (s, 1H), 8.87 (m, 1H), 9.20 (s, 1H). MS (CI) m/z 333 (MH$^+$). Anal. Calcd. for C$_{18}$H$_{16}$N$_6$O: C, H, N.

Pyrazine-2-carboxylic acid N'(7-fluoropyrrolo[1,2-α]quinoxalin-4-yl)-hydrazide 4 (SC144). Following a procedure identical to that described for compound 3, but using 7-fluoro-4-hydrazinopyrrolo[1,2-α]quinoxaline 14c (108 mg, 0.50 mmol), compound 4 was obtained as a pale yellow solid (56 mg, 35% yield); mp 196° C. (methanol/ethyl acetate); IR (KBr) 3255, 1690 cm$^{-1}$; $^1$H NMR (DMSO-d$_6$) 6.75 (m, 1H), 7.15 (m, 1H), 7.37 (bs, 1H), 7.61 (m, 2H), 8.15 (m, 1H), 8.31 (m, 1H), 8.87 (s, 1H), 8.97 (m, 1H), 9.26 (s, 1H), 11.50 (bs, 1H, exch. with D$_2$O). MS (CI) m/z 323 (MH$^+$). Anal. Calcd. for C$_{16}$H$_{11}$FN$_6$O: C, H, N.

N'-Imidazo[1,2-α]pyrido[3,2-e]pyrazin-6-ylpyrazine-2-carbohydrazide 5 (SC148). Following a procedure identical to that described for compound 3, but using 6-hydrazinoimidazo[1,2-α]pyrido[3,2-e]pyrazine 14d (100 mg, 0.50 mmol), compound 5 was obtained as a pale yellow solid (38 mg, 25% yield); mp 271° C. (methanol); IR (KBr) 3250, 1675 cm$^{-1}$; $^1$H NMR (DMSO-d$_6$) 7.52 (m, 1H), 7.76 (s, 1H), 8.02 (m, 1H), 8.41 (s, 1H), 8.57 (s, 1H), 8.85 (s, 1H), 8.96 (s, 1H), 9.26 (s, 1H), 10.76 (bs, 1H), 13.93 (bs, 1H). MS (CI) m/z 307 (MH$^+$). Anal. Calcd. for C$_{14}$H$_{10}$N$_8$O: C, H, N.

General procedure for the preparation of compounds 6-9 (SC 155-158). The preparation of 1H-indole-2-carboxylic acid N'-pyrrolo[1,2-α]quinoxalin-4-yl-hydrazide 6 (SC155) is reported as a representative example.

To a stirred solution of EDC (94 mg, 0.49 mmol) and DMAP (cat.) in ethyl acetate (15 mL), compound 14a (77 mg, 0.39 mmol) and 2-indolecarboxylic acid (63 mg, 0.39 mmol) were added, portion wise, within 15 minutes. The resulting mixture was stirred at room temperature for 24 h, then shaken with sodium bicarbonate saturated solution and water. Evaporation of the dried extract gave a residue which was crystallized to give compound 6 as a white solid (82 mg, 62% yield); mp 186° C. (dichloromethane/light petroleum); IR (KBr) 3255, 1680 cm$^{-1}$; $^1$H NMR (DMSO-d$_6$) 6.75 (s, 1H), 7.05 (m, 1H), 7.20 (m, 4H), 7.40 (m, 3H), 7.65 (m, 1H), 8.10 (m, 1H), 8.35 (s, 1H), 9.55 (bs, 1H), 10.65 (bs, 1H), 11.80 (bs, 1 H). MS (CI) m/z 342 (MH$^+$). Anal. Calcd. for C$_{20}$H$_{15}$N$_5$O: C, H, N.

1H-Indole-5carboxylic acid N'-pyrrolo[1,2-α]quinoxalin-4-yl-hydrazide 7 SC156. Following a procedure identical to that described for compound 6, but using 2-indolecarboxylic acid (63 mg, 0.39 mmol), compound 7 was obtained as a white solid (69 mg, 52% yield); mp 160° C. (dichloromethane/light petroleum); IR (KBr) 3250, 1680 cm$^{-1}$; $^1$H NMR (acetone-d$_6$) 6.60 (d, 1H, J=3.6 Hz), 6.75 (t, 1H, J=3.6 Hz), 7.23 (d, 1H, J=3.6 Hz), 7.29 (m, 2H), 7.51 (m, 3H), 7.85 (d, 1H, J=8.5 Hz), 8.03 (m, 1H), 8.20 (m, 1H), 8.39 (s, 1H), 9.60 (bs, 1H), 10.70 (bs, 1H), 11.45 (bs, 1H). MS (CI) m/z 342 (MH$^+$). Anal. Calcd. for C$_{20}$H$_{15}$N$_5$O: C, H, N.

General procedure for the preparation of compounds 10 and 11 (SC153 and SC154). The preparation of compounds 10 and 11 was accomplished by a condensation step, using an EDC/DMAP procedure identical to that described for the preceding compound but using the appropriate N—BOC-aminoacid, followed by deprotection.

1H-Indole-6-carboxylic acid N'-pyrrolo[1,2-α]quinoxalin-4-yl-hydrazide 8 SC157. Following a procedure identical to that described for compound 6, but using 6-indolecarboxylic acid (63 mg, 0.39 mmol), compound 8 was obtained as a white solid (17 mg, 13% yield); mp 198.5° C. (dichloromethane/light petroleum); IR (KBr) 3245, 1685 cm$^{-1}$; $^1$H NMR (acetone-d$_6$) 6.55 (m, 1H), 6.85 (m, 1H), 7.28 (m, 1H), 7.28 (m, 3H), 7.45 (m, 1H), 7.60 (d, 1H, J=8.1 Hz), 8.70 (m, 2H), 8.15 (s, 1H), 8.39 (m, 1H), 9.44 (bs, 1H), 10.55 (bs, 1H), 11.51 (bs, 1H). MS (CI) m/z 342 (MH$^+$). Anal. Calcd. for C$_{20}$H$_{15}$N$_5$O: C, H, N.

1H-Indole-3-carboxylic acid N'-[1,2-α]quinoxalin-4-yl-hydrazide 9 SC158. Following a procedure identical to that described for compound 6, but using 3-indolecarboxylic acid (63 mg, 0.39 mmol), compound 9 was obtained as a white solid (42 mg, 32% yield); mp 162.5° C. (dichloromethane/light petroleum); IR (KBr) 3250, 1685 cm$^{-1}$; $^1$H NMR (CDCl$_3$) 6.80 (m, 1H), 6.90 (t, 1H, J=3.3 Hz), 7.08 (d, 1H, J=3.2 Hz), 7.30-7.60 (m, 4H), 7.48 (m, 1H), 7.58 (m, 1H), 7.90 (m, 2H), 8.10 (m, 1H), 8.11 (s, 1H), 8.30 (m, 1H), 9.20 (bs, 1H), 10.25 (bs, 1H), 11.60 (bs, 1H). MS (CI) m/z 342 (MH$^+$). Anal. Calcd. for C$_{20}$H$_{15}$N$_5$O: C, H, N.

N,N'-Bis-pyrrolo[1,2-α]quinoxaline-4-carbohydrazide 12 (SC147). A mixture of hydrazine monohydrate (22 uL, 0.45 mmol) and ethyl pyrrolo[1,2-α]quinoxaline-4-carboxylate 15 (216 mg, 0.90 mmol) in ethanol (2 mL) was heated to reflux for 3 h. The residue obtained after evaporation of the solvent was purified by chromatography (dichloromethane: ethyl acetate, 9:1) to give compound 12 as a white solid (115 mg, 62% yield); mp 138-139° C. (ethyl acetate/hexane)); IR (KBr) 1680 cm$^{-1}$; $^1$H NMR (DMSO-d$_6$) 6.28 (d, 2 H, J=1.7 Hz), 7.01 (d, 2H, J=1.7 Hz), 7.45 (m, 8H), 7.95 (d, 2H, J=7.5 Hz), 9.95 (bs, 1H), 10.80 (bs, 1H). MS (CI) m/z 421 (MH$^+$). Anal. Calcd. for C$_{24}$H$_{16}$N$_6$O$_2$: C, H, N.

Thiazolidine-4-carboxylic acid N'-pyrrrolo-[1,2-α]-4-yl-hydrazide 10 (SC153). Starting from N—BOC-thiazolidine-4-carboxylic acid (90 mg, 0.39 mmol), tert-butyl 4-1,3-thiazolidine-3-carboxylate was obtained as a solid, after crystallization (hexanes), and directly used for the subsequent hydrolytic step. The solid obtained was added to a stirred mixture of TFA (2 mL) and anisole (2 mL) at 0° C. The reaction mixture was allowed to reach to room temperature and stirred for a further 50 minutes. Evaporation of the volatiles by azeotropization with toluene (3×3 mL) gave compound 10 as a pale yellow solid (66 mg, 55% yield based on 14a); mp 162° C. (ethyl acetate/hexanes); IR (KBr) 3255, 1690 cm$^{-1}$; $^1$H NMR (methanol-d$_4$) 3.15 (dd, 1H, J=10.9, 4.9) 3.30 (dd, 1H, J=10.9, 7.1 Hz), 4.11 (0.5 of ABq, 1H, J=9.7 Hz), 4.25 (0.5 of ABq, 1H, J=9.7 Hz), 4.45 (dd, 1H, J=7.1, 4.9 Hz), 6.92 (m, 1H), 7.41 (m, 3H), 7.71 (d, 1H, J=7.4 Hz), 8.09 (d, 1H, J=9.3 Hz), 8.38 (m, 1H), 10.40 (bs, 1H), 11.20 (bs, 1H). MS (CI) m/z 314 (MH$^+$). Anal. Calcd. for C$_{15}$H$_{15}$N$_5$OS: C, H, N.

3-Amino-propionic acid N'-pyrrolo[1,2-α]quinoxalin-4-yl-hydrazide 11 SC154. Following a procedure identical to that described for compound 10, but using N—BOC-β-alanine (74 mg, 0.39 mmol), compound 11 was obtained as a white solid (92 mg, 88% yield based on 14a); mp 164.5° C. (dichloromethane/light petroleum); IR (KBr) 3255, 1680 cm$^{-1}$; $^1$H NMR (DMSO-d$_6$) 2.80 (m, 2H) 3.20 (m, 2H), 7.05 (m, 1H), 7.50 (m, 2H), 7.95 (m, 2H), 8.30 (m, 1H), 8.60 (m, 1H), 10.70 (bs, 1H), 11.25 (bs, 1H). MS (CI) m/z 270 (MH$^+$). Anal. Calcd. for C$_{14}$H$_{15}$N$_5$O: C, H, N.

3-Amino-3-(2-chlorophenyl)-propionic acid N'-pyrrolo[1,2-a]quinoxalin-4-yl-hydrazide (SC160). To a stirred solution of EDC (94 mg, 0.49 mmol) and DMAP (cat.) in ethyl acetate (15 mL), 4-hydrazinopyrrolo[1,2-a]quinoxaline 14a (77 mg, 0.39 mmol) and Boc-3-amino-3-(2-chlorophenyl)propionic acid (78 mg, 0.39 mmol) were added, portion wise over 15 minutes period. The resulting mixture was stirred at room temperature for 24 h, then shaken with sodium bicarbonate saturated solution and water. Evaporation of the dried extract gave a residue which was purified by crystallization and used for the subsequent hydrolytic step without further characterization. The solid obtained was added to a stirred mixture of TFA (2 mL) and anisole (2 mL) at 0° C. The reaction mixture was allowed to reach to room temperature and stirred for an additional 50 minutes. Evaporation of the volatiles by azeotropization with toluene (3×3 mL) gave the title compound as a solid.

Quinoxaline-2-carboxylic acid N'-pyrrolo[1,2-α]quinoxalin-4-yl-hydrazide SC 173. To a stirred suspension of 2-quinoxalinecarboxylic acid (87 mg, 0.50 mmol) in dry dichloromethane (2 mL) were added, portion wise, within 1 h, triphenylphosphine (262 mg, 1.00 mmol) and 2,2'-dipyridyl disulfide (220 mg, 1.00 mmol). When the starting material disappeared (TLC) a solution of 4-hydrazinopyrrolo[1,2-a]quinoxaline 14a (100 mg, 0.50 mmol) in the same solvent (6 mL) was added and the resulting mixture was stirred at room temperature overnight. The solvent was removed and the residue was partitioned between ethyl acetate and water. The organic layer was separated, shaken with brine and dried. The residue left after evaporation of the solvent was purified by flash-chromatography to afford the title compound as a solid.

Nicotinic acid N'-9H-pyrrolo[1,2-α]indol-9-yl-hydrazide SC 175. Solid nicotinoyl chloride hydrochloride (155 mg, 0.90 mmol) was added portion wise to a stirred and ice-cooled solution of 9-hydrazino-9H-pyrrolo[1,2-α]indole (187 mg, 1.01 mmol) in dry pyridine (15 mL). The mixture was stirred overnight at room temperature. After evaporation of the volatiles, the title compound was isolated as a solid which was purified by column chromatography or crystallization.

SC144 Shows Remarkable Potency Against a Panel of Hormone-Dependent and -Independent Cell Lines.

The sensitivity of a panel of seven human cancer cell lines to SC144 was assessed by MTT-assay. SC144 showed an excellent activity with $CC_{50}$ dose range of 0.7 to 10 uM (Table 1). The sensitivity towards SC144 was time- and dose-dependent. The activity of SC144 in these cell lines appeared to be independent of HR, p53, pRb, p21 and p16 status (Table 1). SC144 showed a remarkable activity in HEY cells ($CC_{50}$=1.0±0.06 uM) considering that this cell line appears to be practically resistant to cisplatin, the most commonly used drug in ovarian cancer. Moreover, SC144 was ten-fold more potent in HEY cells than in the prostate cancer PC3 cell line ($CC_{50}$=10.0±0.2 uM). SC144 also exhibited a good activity in HR positive (MCF-7 and MDA-MB-468) and negative (MDA-MB-435) human breast cancer cells. Interestingly, the ER+ cells exhibited a 5.5-fold (MDA-MB-468, $CC_{50}$=0.7±0.1 uM) and 2.3-fold (MCF-7, $CC_{50}$=1.7±0.3 uM) more sensitivity to SC144 than the ER-cell line (MDA-MB-435, $CC_{50}$=4.0±1.4 uM) (Table 1).

TABLE 1

Sensitivity of prostate, breast and ovarian cancer cell lines to SC144

| Cell line | Origin | [b]HR | p53 | pRb | p16 | p21 | [a]$CC_{50}$ values (mean ± SD) SC144 (μM) |
|---|---|---|---|---|---|---|---|
| PC3 | Prostate | AR− | Null | WT | WT | WT | 10 ± 0.2 |
| DU145 | Prostate | AR− | Mut | Null | Mut | Mut | 3.0 ± 0.3 |
| HEY | Ovarian | AR+ | WT | ND | WT | ND | 1.0 ± 0.1 |
| MCF-7 | Breast | ER+ | WT | WT | WT | WT | 2.0 ± 0.3 |
| MCF-7/ADR | Breast | ER− | Mut | WT | ND | WT | 2.5 ± 1.0 |
| MDA-MB-435 | Breast | ER− | Mut | WT | WT | WT | 4.0 ± 0.1 |
| MDA-MB-468 | Breast | ER− | Mut | Null | ND | WT | 0.7 ± 0.1 |

[a]$CC_{50}$ is defined as drug concentration causing a 50% decrease in cell population;
[b]HR: hormone receptor; AR: androgen receptor; ER: estrogen receptor; WT: wild-type; Mut: mutated; ND: not-determined. HEY cells are resistant to cisplatin and MCF/ADR cells are resistant to doxorubicin.

SC144 Treatment Induces S-Phase Arrest.

Cell cycle perturbations induced by SC144 were examined in HEY and MDA-MB-435 cells. The analysis of DNA profiles by flow cytometry indicated that SC144 induced S-phase arrest comparable to that of camptothecin (CPT). As shown in FIG. 1, 80% of the cells were retained in S-phase after 24 h of treatment with SC144 (3 uM). Similar effects were obtained on the asynchronus prostate cancer cell line DU145. The maximum arrest was observed at 24 h of SC144 exposure, which was sustained up to 48 h. This property of SC144 to induce cell cycle arrest makes it an ideal agent for combination therapy with other agents that act at different stages of cell cycle, such as taxanes.

SC144 Treatment Induces Apoptosis.

Figure 2:
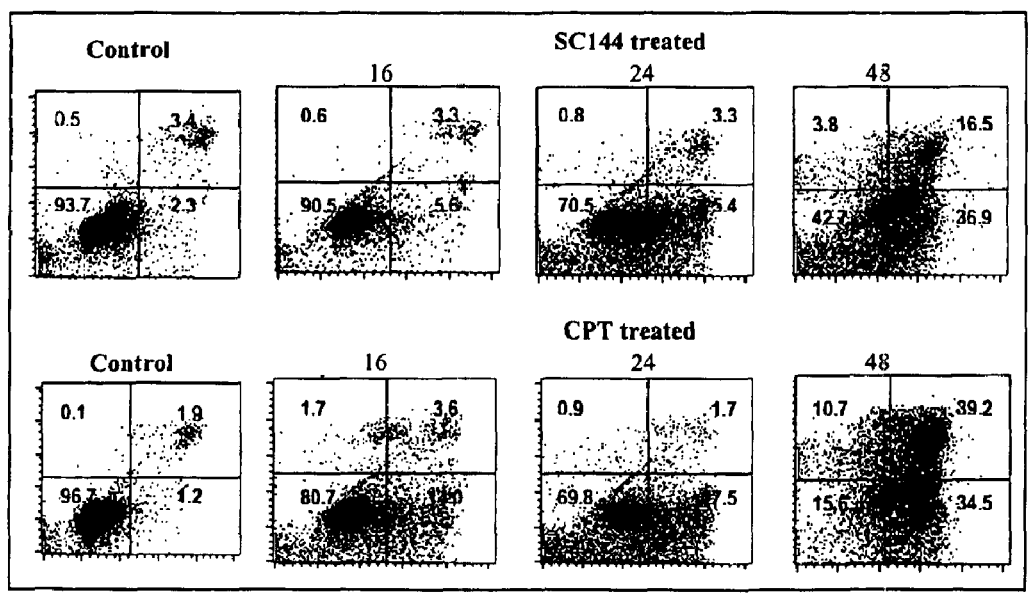
FIG. 2 illustrates apoptosis analysis of MDA-MB-435 cells treated with SC144 and CPT ($IC_{80}$). Cells were stained with annexin V/PI and analyzed by flow cytometry. Cells in the bottom left quadrant of each panel (Annexin V-negative, PI-negative) are viable, whereas cells in the bottom right quadrant (Annexin V-positive, PI-negative) are in the early stages of apoptosis, and cells in the top right quadrant (Annexin V-positive, PI-positive) are in later stages of apoptosis and necrosis.

An early event in apoptotic cell death is the translocation of the phosphatidyl-serine residues to the outer part of the cell membrane. This event precedes nuclear breakdown, DNA fragmentation, the appearance of most apoptosis-associated molecules, and is readily measured by annexin V binding assay. By this method, SC144 was compared with CPT. As shown in FIG. 2, SC144 caused a very strong apoptotic effect comparable to that induced by CPT. The percentage of early-apoptotic cells increased in treated cells reaching 37% and 34% at 48 h for SC144 and CPT, respectively. At 48 h an increase in late-apoptosis/necrosis was also observed for both compounds (16% and 39% for SC144 and CPT, respectively).

SC144 Shows In Vivo Efficacy in Mice Xenograft Models.

Figure 3A:
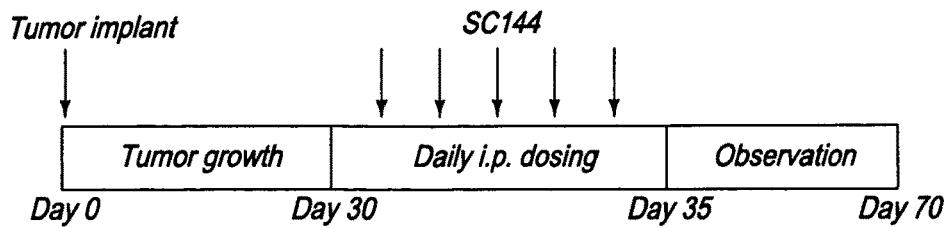
FIG. 3. (A) is a schematic outline of tumor growth and dosing in xenograft models. Athymic nude mice implanted with MDA-MB-435 cells were treated with the indicated doses of SC144 by daily i.p. administration for five-days. (B) illustrates that SC144 reduced the size of human breast cancer xenografts at doses of 0.3, 0.8 and 4 mg/kg. Tumor growth was monitored for five weeks. Values represent the median tumor weight for each group. (C) shows % T/C for each treatment group calculated on the last day of experiment (bars±SD).
Figure 3B:
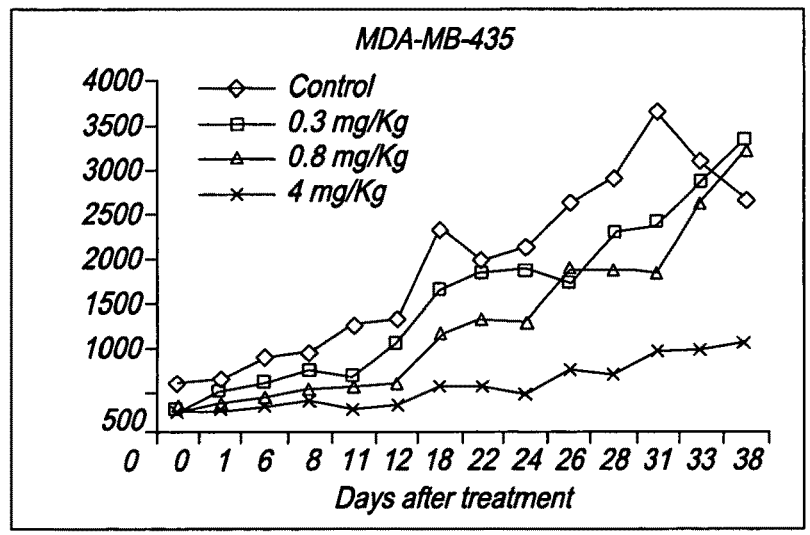

The in vivo efficacy of SC144 was evaluated in a nude mice xenograft model of human breast MDA-MB-435 cells. A schematic outline of the experimental procedure is shown in FIG. 3A. Animals were treated with daily i.p. injections of saline (controls) and SC144 at 0.3 mg/kg, 0.8 mg/kg and 4 mg/kg. After five-days of dosing, the drug treatment was discontinued and the animals were monitored bi-weekly for five weeks. FIG. 3B shows the volume (mean±SD) for SC144 treated MDA-MB-435 xenografts over time.

Figure 3C:
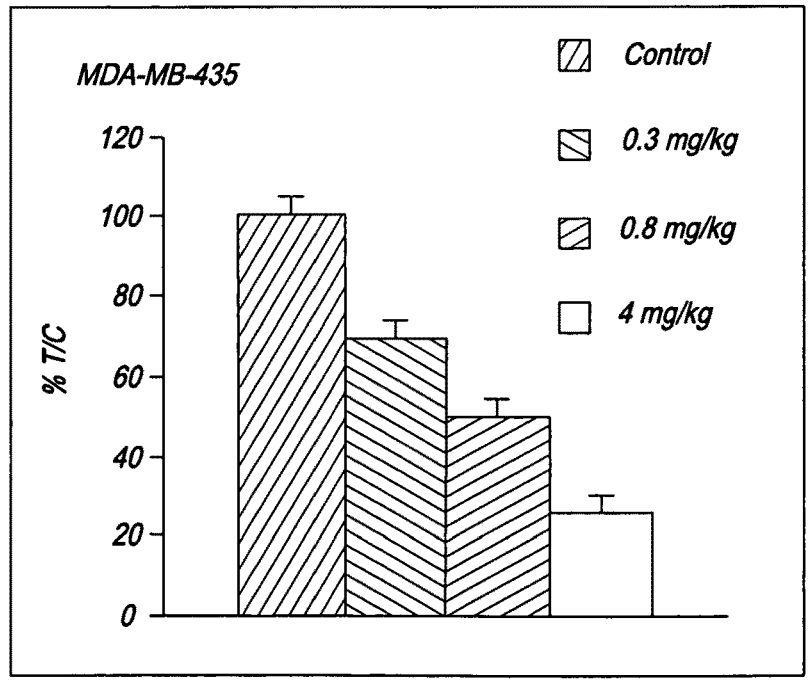

For statistical analysis, the % T/C value was calculated on the last day of dosing and is graphed for all of the treatment groups (FIG. 3C). A marginal reduction was observed at the lowest dose of SC144 in breast cancer xenografts. Significant reduction in tumor growth was observed at higher SC144 doses. SC144 reduced tumor growth by 60% at 4 mg/kg. Representative images of mice with and without SC144 treatment at the end of the study is shown in FIG. 4A. Whereas in control mice, tumor mass became bulky, spread around the chest cavity, and densely vascularized, the SC144 treated tumors were markedly decreased in size, poorly vascularized, and remained localized (FIGS. 4, B and C). Treatment with SC144 was well tolerated and did not result in drug-related deaths. Furthermore, no changes in body weight compared to vehicle control were observed with SC144.

The studies were expanded to other cell lines. It was found that SC144 shows nanomolar potency in non-small cell lung cancer cells HOP-62, EKVX, and HOP-92. The $CC_{50}$ values range from 10-20 nM, which is about 400-fold more potent than the MDA-MB-435 cell line (Table 2). Subnanomolar to low nanomolar potency was also observed in HCT-116 and HT29 colon cancer cell lines (Table 2).

TABLE 2

Sensitivity of various cancer cells to SC144

| Cell line | Origin | $CC_{50}$ (uM) |
|---|---|---|
| HOP-62 | Non-small cell lung cancer | 0.01 |
| HOP-92 | Non-small cell lung cancer | 0.2 |
| EKVX | Non-small cell lung cancer | 0.01 |
| HL60 | Leukemia | 0.27 |
| RPMI-8226 | Leukemia | 0.25 |
| SF-268 | CNS cancer | 0.3 |
| SF-295 | CNS | 0.42 |
| UACC-257 | Melanoma | 0.4 |
| UACC-62 | Melanoma | 0.8 |
| SKOV3 | Ovarian cancer | 0.12 |
| UO-31 | Renal cancer | 0.3 |
| HCT-116 | Colon | 0.017 |
| HT29 | Colon | 0.078 |

SC144 Induce a Selective and Remarkable Tumor Necrosis In Vivo.

Figure 5:
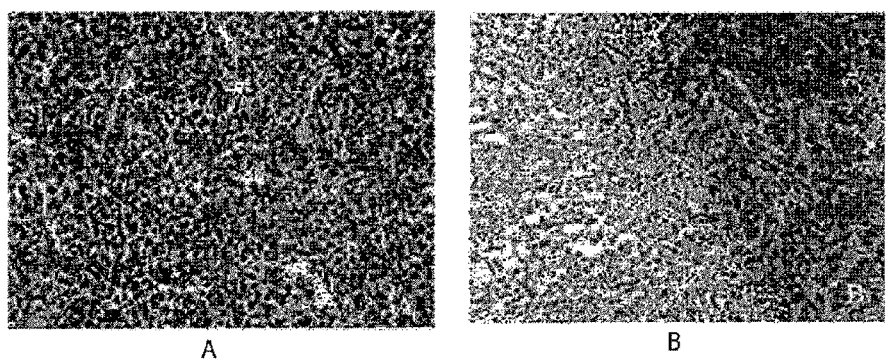
FIG. 5 demonstrates that SC144 induce remarkable necrosis of tumor tissue. H&E staining of untreated tumor tissue (A) and SC144 treated tissue (B) were prepared at day 70. In general, greater than 80% necrosis was observed in treated tumors (left side of panel B) and the non-necrotic cells (right side of panel B) are in early stages of apoptosis.

To evaluate the extent of tumor necrosis after drug treatment tumor samples were collected from control and treated mice on day 70. FIG. 5 shows an H&E staining of tumor samples from a representative mouse. In general, greater than 80% necrosis of tumor tissues treated with 4 mg/kg of SC144 was observed (FIG. 5B).

SC144 Does Not Exhibit Systemic Toxicity.

Figure 6:
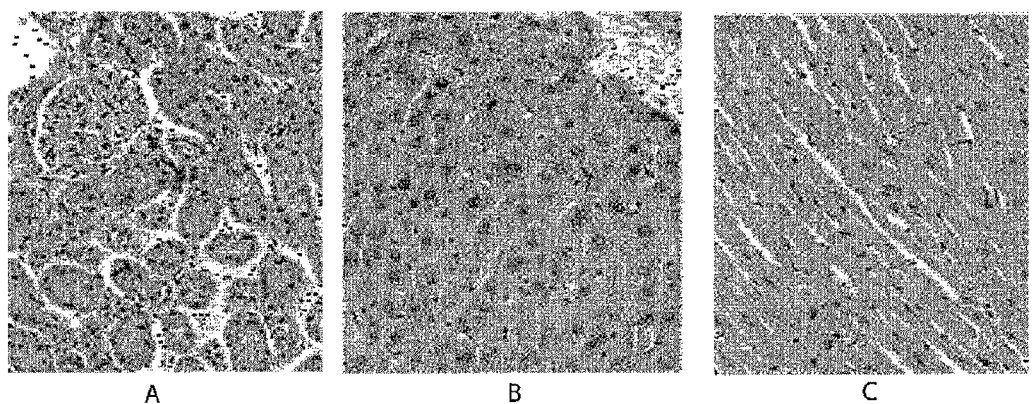
FIG. 6 demonstrates that SC144 does not exhibit organ toxicity. H&E staining of SC144 treated kidney tissue (A), liver tissue (B) and cardiac tissue (C) shows normal pattern.

To evaluate the possibility for systemic toxicity of the SC144, several organs were examined microscopically. FIG. 6 shows representative H&E staining of kidney, liver, and heart tissues from mice treated with 4 mg/kg injection of SC144. No necrosis of glomeruli or tubular necrosis of the kidney was observed (FIG. 6A). No significant pathology of liver tissues was observed. FIG. 6B shows cords of hepatocytes are normal. Finally, cardiac muscles were normal and no detectable damage could be observed (FIG. 6C). In summary, the H&E staining results demonstrate that there was no damage in these organs of the representative mice of each group.

SC144 Does Not Inhibit Cytochrome P450 Enzymes at Concentrations Relevant to Its Antitumor Activity.

Figure 7:
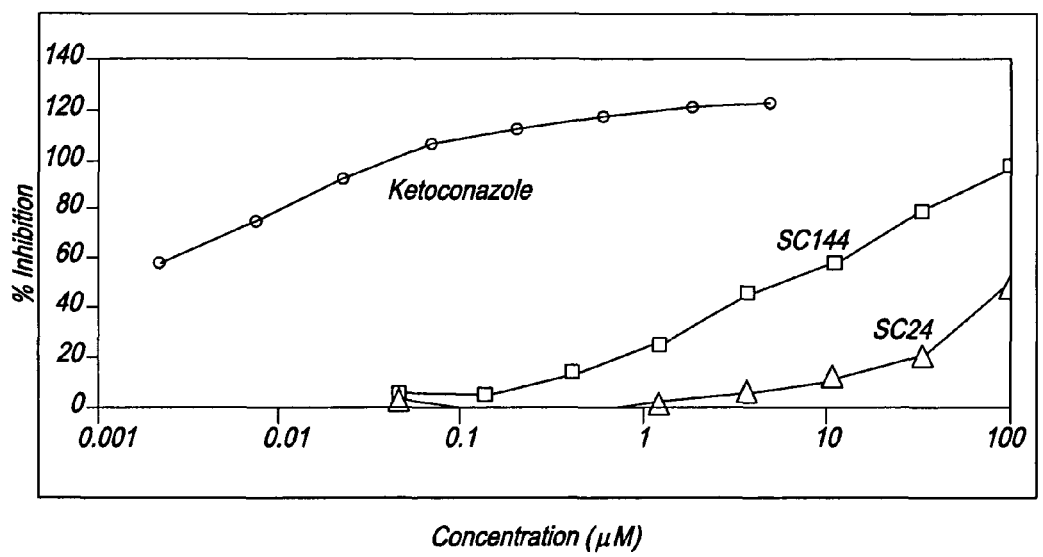
FIG. 7 illustrates inhibition of human CYP3A4 by ketoconazole, SC144 and its analog SC24. The metabolism of fluorescent substrates by human cDNA-expressed CYP3A4 was assessed by incubation in 96 well plate at 37° C. Metabolism of 7-benzyloxy-4-trifluoromethylcoumarin (BFC) was assayed by measuring the production of the corresponding 7-hydroxy-4-trifluoro-methylcoumarin.

The investigation of cytochrome P450 enzyme inhibition by potential drug candidates can aid in predicting drug-drug interactions and/or unfavorable PK profiles produced upon dosing. Competitive inhibition of drug metabolism mediated by important cytochrome P450 enzymes may result in undesirable elevations in plasma drug concentrations, which is of clinical importance for both therapeutic and toxicological reasons. To determine if SC144 inhibits human cytochrome P450 catalytic activity an in vitro assay specific for CYP3A4 comparing to ketoconazole, a well-known substrate as a control, was performed (FIG. 7). These results suggest that SC24, an analogue of SC144, does not significantly inhibit CYP3A4 activity, but SC144 had an $IC_{50}$ value range 8-20 μM, suggesting some CYP3A4 inhibitory activity. However, this concentration is above its antitumor efficacy.

Monitoring Tumor Response to SC144.

[$^{18}$F]FDG is currently the most widely used radiotracer for imaging therapy response in oncology with PET. PET/[$^{18}$F] FDG measures viable cell density in tumors and also provides information on the expression of glucose transporters and hexokinase activity. FMAU labeled with C-11 (20 min half life) is also effective for imaging tumor cell division with PET (Bading et al. (2004) Nucl. Med. Biol. 31:407-418). Following cellular uptake, FMAU is phosphorylated by thymidine kinase and incorporated into DNA. Preliminary studies with this technology have indicated that it is well suited for following the effects of SC144 in a mouse human tumor xenograft model.

The baseline, equilibrium-phase FDG scan shows a viable tumor on the right shoulder of the mouse (arrow). Early on (FIG. 8B), FMAU shows a "hot" rim surrounding the tumor, suggesting a poorly perfused center. In later images at 30 and 60 min (FIG. 8C), FMAU had filled up the whole tumor, indicating the presence of dividing cells throughout.

Figure 8:
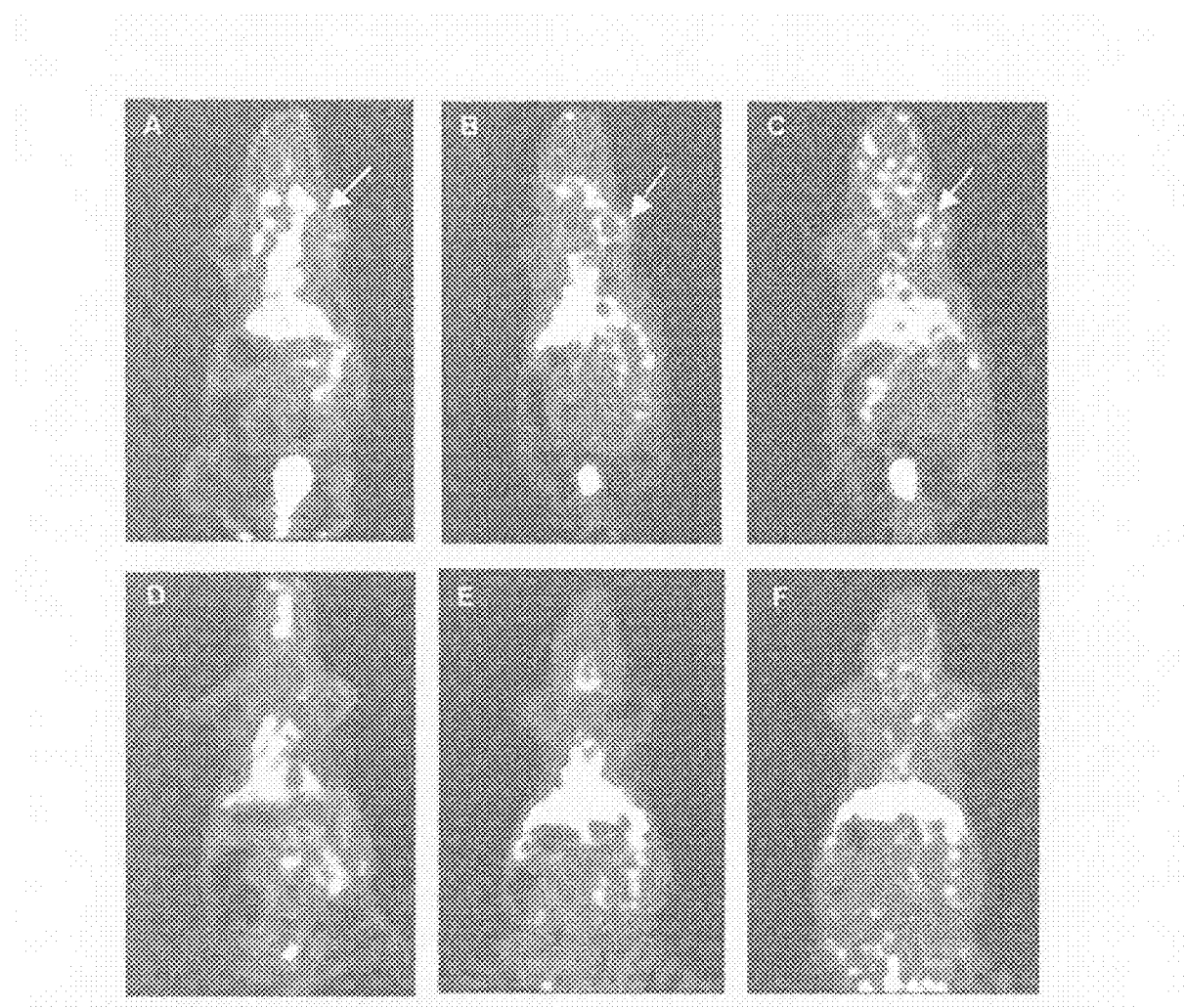
FIG. 8 shows PET imaging (slice thickness 0.6 mm) of a nude mouse implanted with human breast cancer (MDA-MB-435) cells. Top row, baseline scans: (A) equilibrium-phase FDG, 30 min post injection; (B) FMAU, 10 min post injection; (C) FMAU, 60 min post injection. Bottom row, follow-up scans: (D) FDG, 30 min post injection; (E) FMAU, 10 min post injection; (F) FMAU, 60 min post injection. The mouse was imaged on consecutive days with FDG and FMAU (baseline), then treated with daily i.p. injections of SC144 at 4 mg/kg. After five days of dosing, the drug treatment was discontinued and the follow-up scans were obtained on days 6 and 7.

FIGS. 8D-F show a repeat study of the same mouse after 5 days of treatment. The FDG scan shows that the tumor has grown considerably (measured volume more than doubled), but now has a necrotic center, consistent with the hypoperfusion seen in the baseline FMAU study. The FMAU scan (FIG. 8E) shows a completely hypoperfused tumor at 10 min. However, the tumor pretty much fills up with FMAU by 60 min, suggesting the continued presence of dividing cells throughout the tumor. Caliper measurements of tumor size were continued for 5 weeks in this mouse and showed a marked (>50%) long-term reduction of tumor volume compared with sham-treated control mice.

The preliminary studies have demonstrated the ability to perform serial microPET studies with [$^{18}$F]FDG and [$^{11}$C] FMAU in xenografted mice treated with SC144. Interestingly, it has been observed that 5 days of SC144 appears to inhibit tumor perfusion, suggesting a possible anti-angiogenic effect.

Comparison of SC Compounds with Drugs with Known Mechanisms.

Six drugs with known mechanisms of action and mechanisms of cell cycle regulations (Table 3) were selected to compare to three SC compounds. Initially, the cytotoxic concentration 50% and 80% $CC_{50}$ and $CC_{80}$ values of all these drugs were determined using MTT assay under a continuous drug exposure for 48 hours (Table 3). For gene expression analysis, MDA-MB-435 cells (1×10$^6$) were treated with the $CC_{80}$ of drugs for 24 hours. The $CC_{80}$ at 24 h value was selected as a single concentration and a single time point because of the prior experience with gene expression analysis using Real-Time PCR studies where it was found that under this condition a significant number of genes could be consistently and reproducibly altered in response to treatment. The goal was to identify patterns of change in gene expression that are characteristic of different classes of drugs, distinct from patterns of final common pathway changes associated with apoptotic or non-apoptotic cell death.

TABLE 3

Activities and profile of drugs used in this study

| Drug | Mechanism of action | Cell cycle profile | $CC_{50}$ (μM) | $CC_{80}$ (μM) |
| --- | --- | --- | --- | --- |
| SC144 | Unknown | S-phase | 4 ± 1.4 | 10 ± 0.01 |
| SC23 | Unknown | $G_0/G_1$ and S-phase | 0.04 ± 0.007 | 0.1 ± 0.01 |
| SC24 | Unknown | $G_0/G_1$ | 0.24 ± 0.03 | 0.97 ± 0.15 |
| Etoposide | Topoisomerase II inhibitor | $G_2/M$ | 52.5 ± 3.5 | 300 ± 106 |
| Mitoxantrone | Topoisomerase II inhibitor | $G_2/M$ | 4.5 ± 1.4 | 7.3 ± 0.35 |
| Camptothecin | Topoisomerase I inhibitor | S and $G_2/M$ | 0.03 ± 0.002 | 0.1 ± 0.002 |
| Cisplatin | DNA alkylating agent | | 39 ± 1.41 | 71 ± 1.4 |
| Taxol | Microtubule stabilizer | M-phase | 0.04 ± 0.003 | 0.07 ± 0.01 |
| 5-Fluorouracil (5FU) | Thymidylate synthase inhibitor | S-phase | 29 ± 10.7 | 100 ± 0.01 |

Bioinformatic Analysis.

Figure 9:
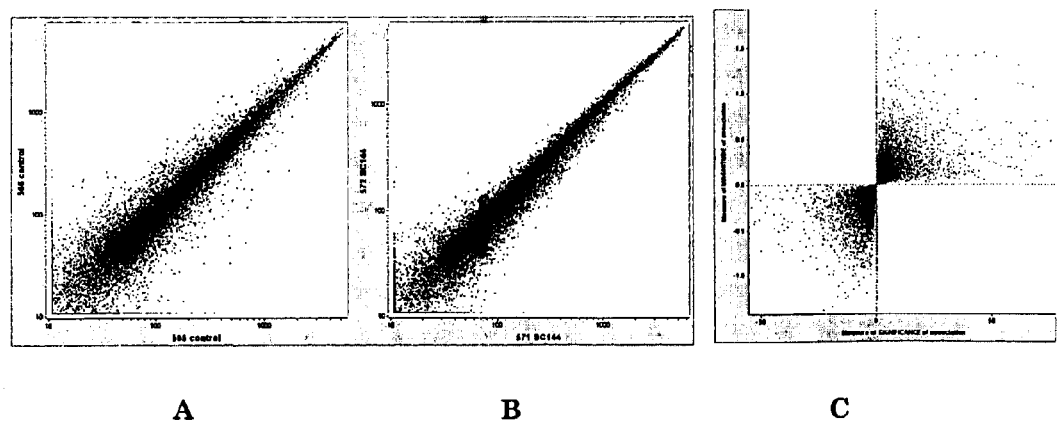
FIG. 9 illustrates comparison of gene expression profiles in two independent experiments. (A) A scatter plot of untreated control samples D565 versus D566 and (B) SC144 treated pairs D571 and D572 Chips. (C) A plot of t-statistic (x-axis), representing the significance level, versus log mean expression difference (representing fold change) in SC144 treated cells versus untreated control.
Figure 10:
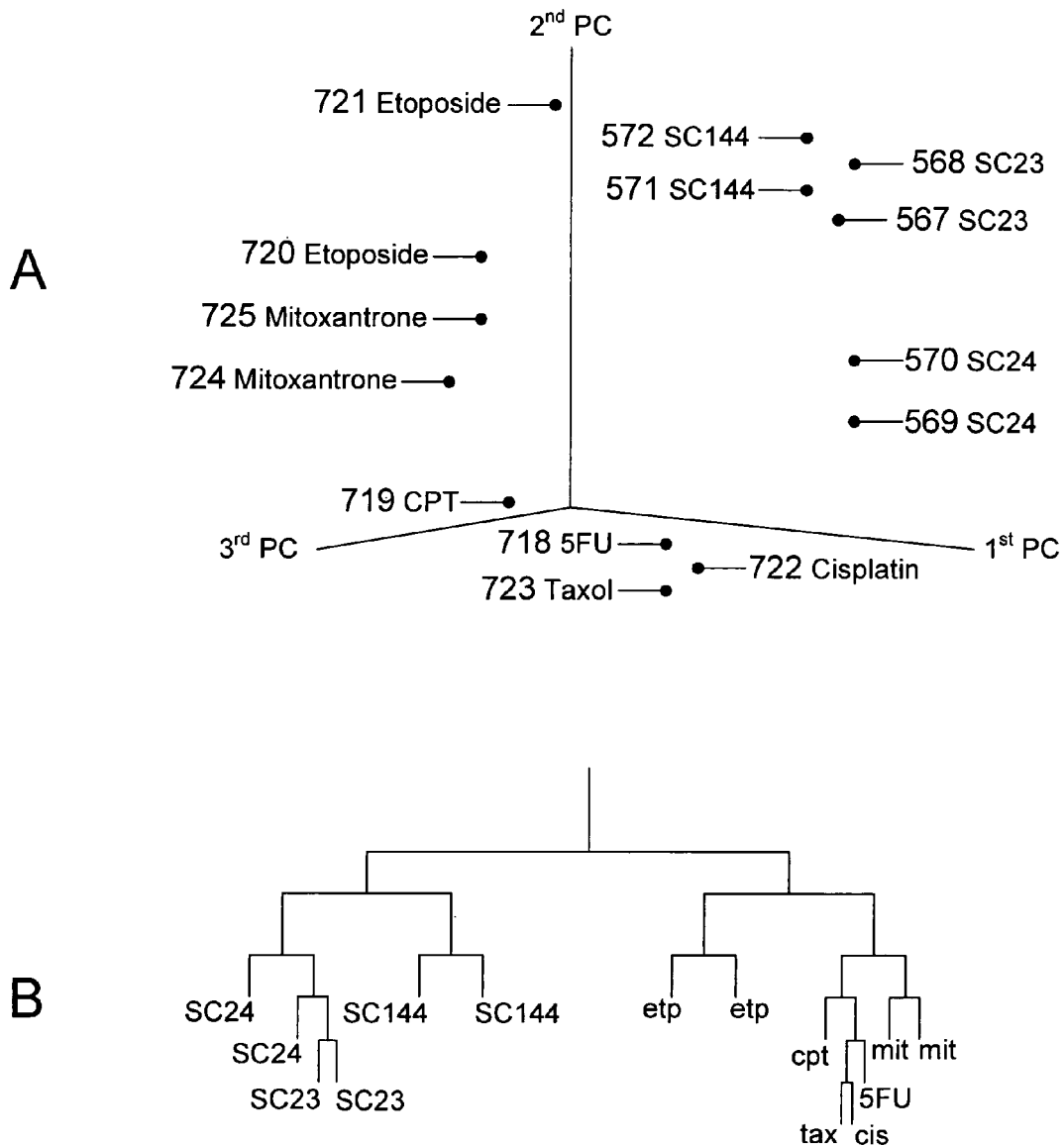
FIG. 10 illustrates that SC144 shows a unique pattern of activity distinct from other classes of compounds. (A) A three-principal components analysis of genes for all 14 observations and (B) hierarchical cluster analysis generated by Genetrix™.

For profiling gene expression analysis, two independent experiments were used with and without drug treatment using the 57,000 Affymetrix GeneChip (U133+2) array. Expression values were truncated below 10, and log transformed. Initial filtering removed all genes that had expression values less than 50 in more than 10% of samples: below this threshold, there is substantial "noise" in the estimates and many genes showing such low values are probably not expressed at all. By allowing 10% to be very low expressers, for a given gene, inclusion of those genes that were unexpressed in just a single group (such as the control group) was allowed. Data reproducibility was confirmed by observation of high correlations between duplicate experiments (FIGS. 9, A and B). A consequence of the close correlation of duplicate experiments was that these samples tended to cluster together (see FIG. 10).

To identify genes significantly up- or down-regulated in treated samples (compared to controls) t-tests was carried out for each gene and the t-statistic against difference in mean log expression plotted (FIG. 9C). From this plot it is possible to identify genes that simultaneously are statistically significant, at a given threshold p value, and show a fold change above a defined value. Alternatively, a p-value cutoff can be selected to yield a set of genes with a predetermined false discovery rate.

Lists of genes that were substantially (10-fold) up- or down-regulated after exposure to each of the six drugs with known modes of action were obtained (see Table 4 for SC144 regulated genes). The lists were combined to create a set of 753 genes that could be expected to distinguish between the six drugs with known mechanism of action. A principal components analysis of these genes for all 14 observations (the three SC compounds, in duplicate plus six known drugs, two analyzed in duplicate) showed that the duplicates tended to cluster relatively close together, with the two topoisomerase II inhibitors forming one group, the other known drugs forming a second and the three SC compounds making up a distinct third cluster (FIG. 10A).

TABLE 4

A list of most significant genes, with p < 0.0001 and fold change of at least 2 for SC144 versus control

| Gene name | Fold change | p-value |
| --- | --- | --- |
| Small proline-rich protein 1A | 28.28 | 0.00002 |
| GTP binding protein overexpressed in skeletal muscle | 25.84 | 0.00003 |
| Interleukin 24 | 25.83 | 0.00008 |
| Sestrin 2 | 25.73 | 0.00005 |
| Hypothetical protein MGC4504 | 24.88 | 0.00002 |
| Cyclin-dependent kinase inhibitor 1A (p21) | 19.81 | 0.00001 |
| Early growth response 1 | 17.89 | 0.00006 |
| ATPase, H+ transporting, lysosomal 38 kDa, V0 subunit d isoform 2 | 12.81 | <0.00001 |
| AXIN1 up-regulated 1 | 12.45 | <0.00001 |
| Dual specificity phosphatase 5 | 11.65 | <0.00001 |
| Superoxide dismutase 2, mitochondrial | 11.52 | <0.00001 |
| Heparin-binding epidermal growth factor-like growth factor | 9.62 | 0.00008 |
| A disintegrin and metalloproteinase domain 19 (meltrin beta) | 8.5 | 0.00003 |
| Endothelial PAS domain protein 1 | 6.59 | 0.00005 |
| Inositol 1,4,5-triphosphate receptor, type 1 | 5.96 | 0.00005 |
| Tissue factor pathway inhibitor (lipoprotein-associated coagulation inhibitor) | 5.4 | <0.00001 |
| Fibrinogen, gamma polypeptide | 4.9 | <0.00001 |
| RAB20, member RAS oncogene family | 4.87 | <0.00001 |
| Protein kinase, AMP-activated, gamma 2 non-catalytic subunit | 4.78 | 0.00001 |
| Oncostatin M receptor | 4.36 | 0.00008 |
| Cathepsin B | 3.89 | 0.00002 |
| Nuclear factor of kappa light polypeptide gene enhancer in B-cells inhibitor, alpha | 3.78 | <0.00001 |
| BCL2/adenovirus E1B 19 kDa interacting protein 3 | 3.63 | 0.00006 |
| Integrin, beta 3 (platelet glycoprotein IIIa, antigen CD61) | 3.35 | <0.00001 |
| Dual specificity phosphatase 10 | 3.3 | <0.00001 |
| Cell cycle control protein SDP35 | 0.19 | 0.00002 |

TABLE 4-continued

A list of most significant genes, with p < 0.0001 and fold change of
at least 2 for SC144 versus control

| Gene name | Fold change | p-value |
|---|---|---|
| Plexin C1 | 0.19 | 0.00003 |
| Microphthalmia-associated transcription factor | 0.16 | 0.00009 |
| Calpain small subunit 2 | 0.14 | 0.00007 |
| Hypothetical protein DKFZp434L142 | 0.07 | <0.00001 |

This pattern was supported by a hierarchical cluster analysis (distance metric: correlation; method: cluster distance computed as the average distance between points in the two clusters), based on all genes, which clustered the SC compounds separately (FIG. 10B). This provides evidence to support the hypothesis that the SC drugs have a distinct mechanism of action resulting in different downstream molecular effects on cells, and thus their gene expression profiles. There are many genes that can be identified as being distinct from patterns of final common pathway changes associated with apoptotic or non-apoptotic cell death. This further illustrates that some patterns of change in gene expression are characteristic of different classes of drugs and can be distinguished from nonspecific (e.g., stress-sensitive) genes by bioinformatic tools.

The attributes (gene ontology codes, protein classification, pathway membership) of the genes in Table 4 were compared to the attributes of the full data set to determine the features that best characterized this set of genes (FIG. 11).

From this analysis, it is possible to examine subsets of genes with particular properties of interest. One such group is the set of genes with an EGF-like domain (as an InterPro classification). FIG. 12 shows this gene list using Genetrix™.

Another category of interest is the "Subset" category, which represents user-defined gene categorizations. For this analysis, the sets of genes up- or down-regulated at least 10-fold were used for each drug to create six such categories. It can be seen from FIG. 13 that there was a significant overlap between the genes associated with SC144 treatment and the "Etoposide" subset, with 19 genes in common between the two lists (with an odds ratio of 16.1, p<0.0001).

A more detailed analysis that looked at all six genes (FIG. 14) showed that there was also significant overlap with mitoxantrone and CPT.

Taken together, these results indicate that, while SC144 shares some features with the topoisomerase inhibitors (specifically, an overlap in the genes with 10-fold or greater up- or down regulation), all three SC compounds cluster separately from the topoisomerase inhibitors, suggesting that these drugs have a distinct mode of action.

While the foregoing has been described in considerable detail and in terms of preferred embodiments, these are not to be construed as limitations on the disclosure. Modifications and changes that are within the purview of those skilled in the art are intended to fall within the scope of the invention.

What is claimed is:

1. A method of treating a subject having breast cancer, comprising:
   administering to the subject an effective amount of a compound of Formula II,

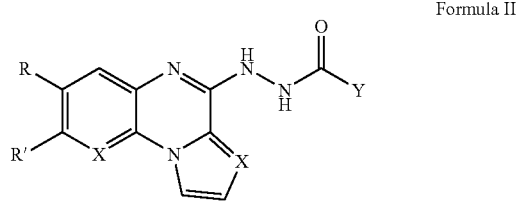

Formula II wherein
R is H, alkyl, or halogen;
R' is H, alkyl, or halogen;
X is CH; and
Y comprises a homocyclic or heterocyclic ring.

2. A method of treating a subject having breast cancer, comprising:
   administering to the subject an effective amount of the compound of Formula II,

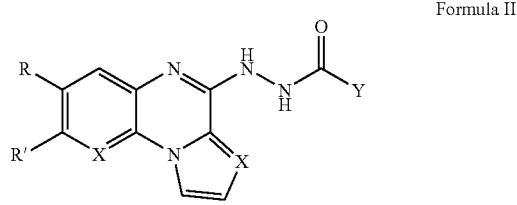

Formula II wherein
R is H, alkyl, or halogen;
R' is H, alkyl, or halogen;
X is CH; and
Y comprises a homocyclic or heterocyclic ring, wherein Y is 2-pyrazinyl or 2-, 3-, 4-pyridinyl.

3. The method of claim 2, wherein the compound is selected from the group consisting of

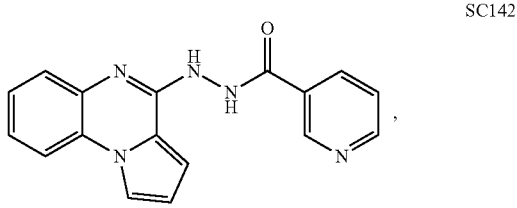

SC142

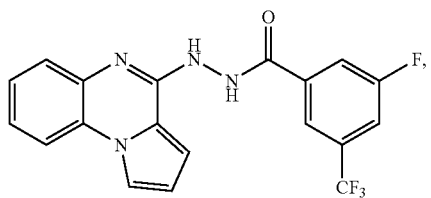
SC169
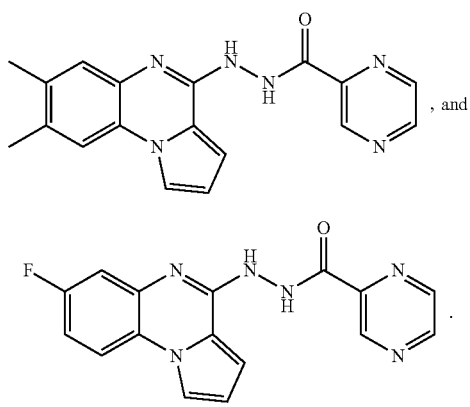
SC143, and
SC144
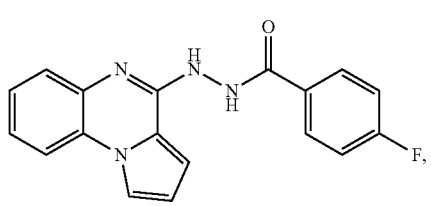
SC170
4. The method of claim 1, wherein the compound is selected from the group consisting of
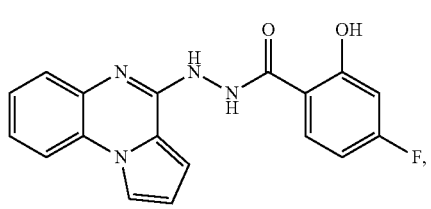
SC171
SC141
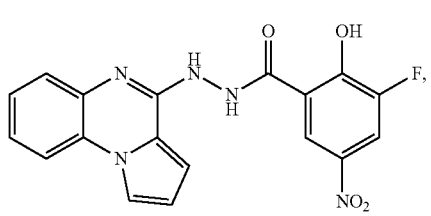
SC172
SC166
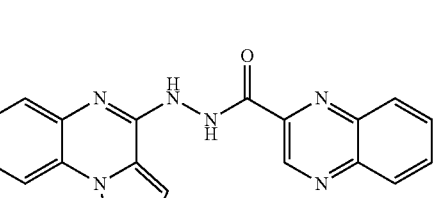
SC173, and
SC167
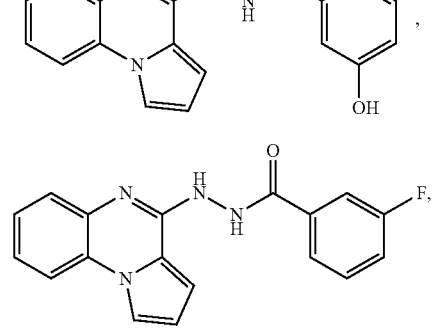
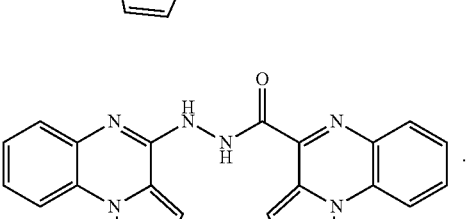
SC174
SC168
* * * * *